(12) United States Patent
Zhang et al.

(10) Patent No.: US 10,048,188 B2
(45) Date of Patent: Aug. 14, 2018

(54) SYSTEM FOR SENSING PARTICULATE MATTER

(71) Applicant: Ford Global Technologies, LLC, Dearborn, MI (US)

(72) Inventors: Xiaogang Zhang, Novi, MI (US); Jianwen James Yi, West Bloomfield, MI (US); David John Kubinski, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 161 days.

(21) Appl. No.: 14/624,228

(22) Filed: Feb. 17, 2015

(65) Prior Publication Data

US 2015/0355067 A1 Dec. 10, 2015

Related U.S. Application Data

(63) Continuation-in-part of application No. 14/299,885, filed on Jun. 9, 2014.

(60) Provisional application No. 62/077,140, filed on Nov. 7, 2014.

(51) Int. Cl.
| | |
|---|---|
| *G01N 15/00* | (2006.01) |
| *G01N 15/06* | (2006.01) |
| *G01M 15/10* | (2006.01) |
| *F01N 13/00* | (2010.01) |
| *F01N 3/20* | (2006.01) |
| *F01N 3/02* | (2006.01) |

(52) U.S. Cl.
CPC ....... *G01N 15/0656* (2013.01); *F01N 13/008* (2013.01); *G01M 15/102* (2013.01); *G01N 15/0606* (2013.01); *F01N 3/02* (2013.01); *F01N 3/20* (2013.01); *F01N 2560/05* (2013.01); *Y02A 50/2322* (2018.01)

(58) Field of Classification Search
CPC .................................................. G01N 15/0656
See application file for complete search history.

(56) References Cited

U.S. PATENT DOCUMENTS

| | | | |
|---|---|---|---|
| 6,634,210 | B1 | 10/2003 | Bosch et al. |
| 6,971,258 | B2 | 12/2005 | Rhodes et al. |
| 7,413,641 | B2 | 8/2008 | Yamada et al. |
| 7,810,375 | B2 | 10/2010 | Weyl et al. |
| 8,341,936 | B2 | 1/2013 | Zhang |
| 8,452,517 | B2 | 5/2013 | Sawada et al. |

(Continued)

OTHER PUBLICATIONS

Leone, T., "Method and System for Secondary Air Injection Coordination with Exhaust Back Pressure Valve," U.S. Appl. No. 14/312,323, filed Jun. 23, 2014, 34 pages.

*Primary Examiner* — Lisa Caputo
*Assistant Examiner* — Alex Devito
(74) *Attorney, Agent, or Firm* — Julia Voutyras; McCoy Russell LLP

(57) ABSTRACT

Systems and methods are described for sensing particulate matter in an exhaust system of a vehicle. An example system comprises a first outer tube with a plurality of intake apertures on an upstream surface, a second inner tube with a plurality of intake apertures on a downstream surface, and a particulate matter sensor placed within the second inner tube. The second inner tube may be positioned within the first outer tube such that a central axis of the second inner tube is parallel to a central axis of the first outer tube.

9 Claims, 14 Drawing Sheets

(56) References Cited

U.S. PATENT DOCUMENTS

| | | |
|---|---|---|
| 2002/0040599 A1* | 4/2002 | Holleboom .......... G01D 11/245 73/431 |
| 2011/0209523 A1* | 9/2011 | Otsubo .............. G01N 27/4077 73/23.31 |
| 2013/0031952 A1 | 2/2013 | Day et al. |
| 2013/0213013 A1 | 8/2013 | Mitchell et al. |
| 2013/0219990 A1 | 8/2013 | Allmendinger et al. |

* cited by examiner

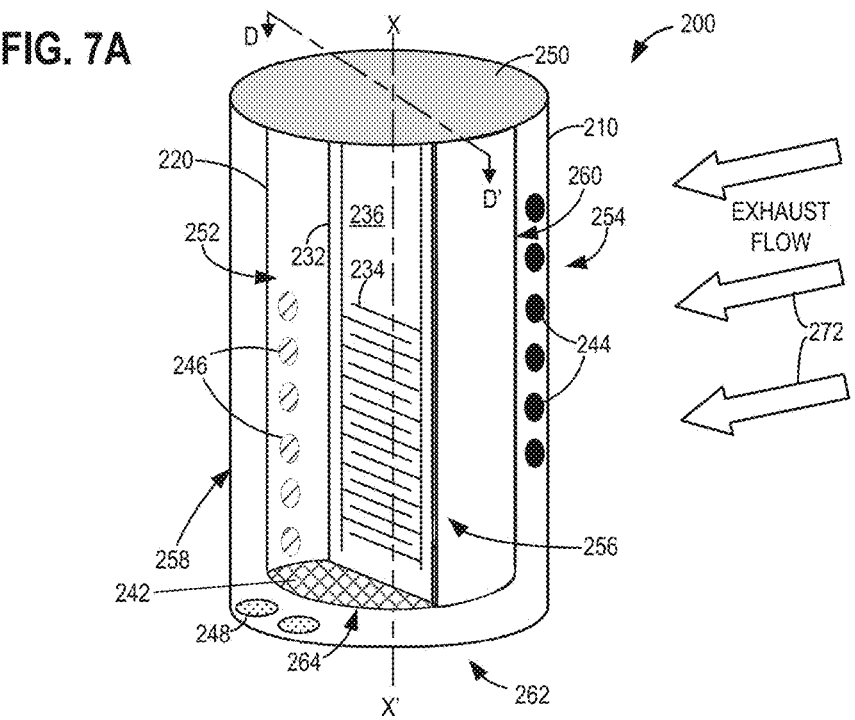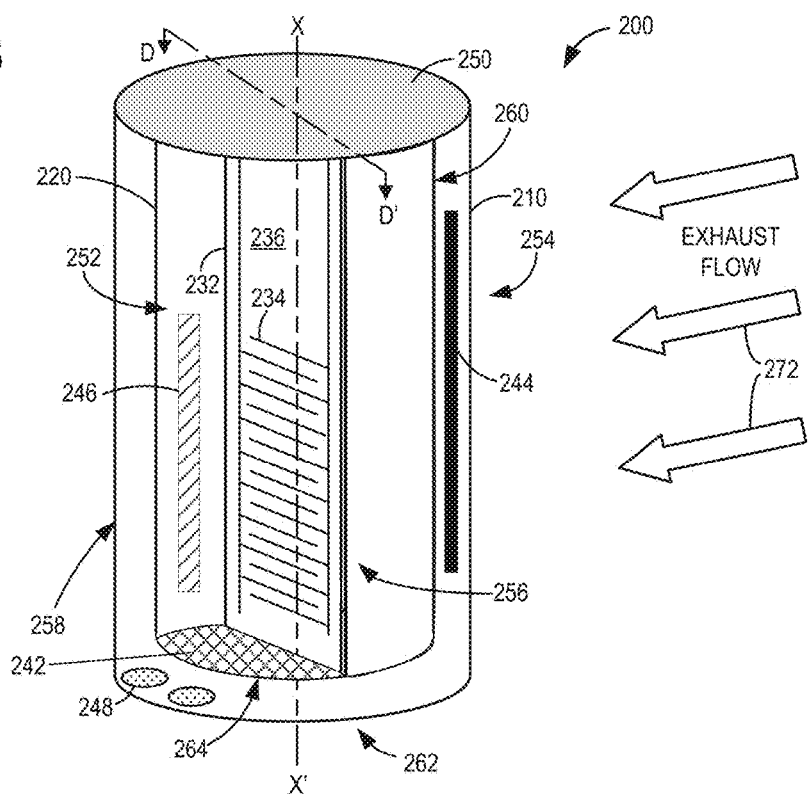

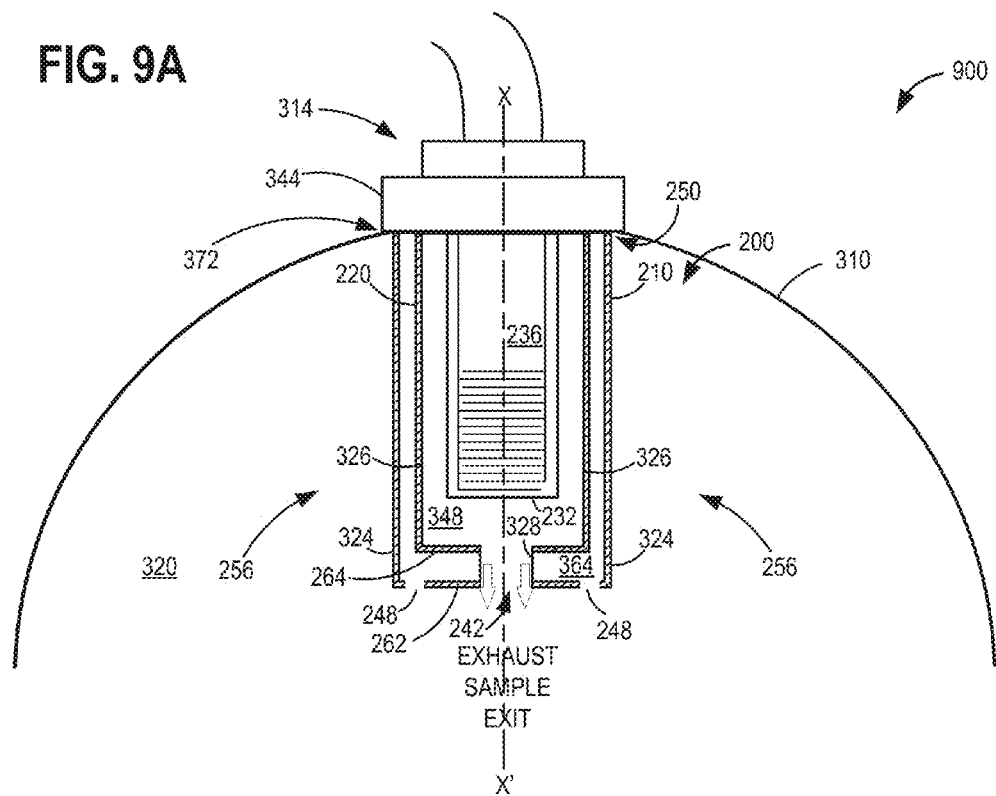
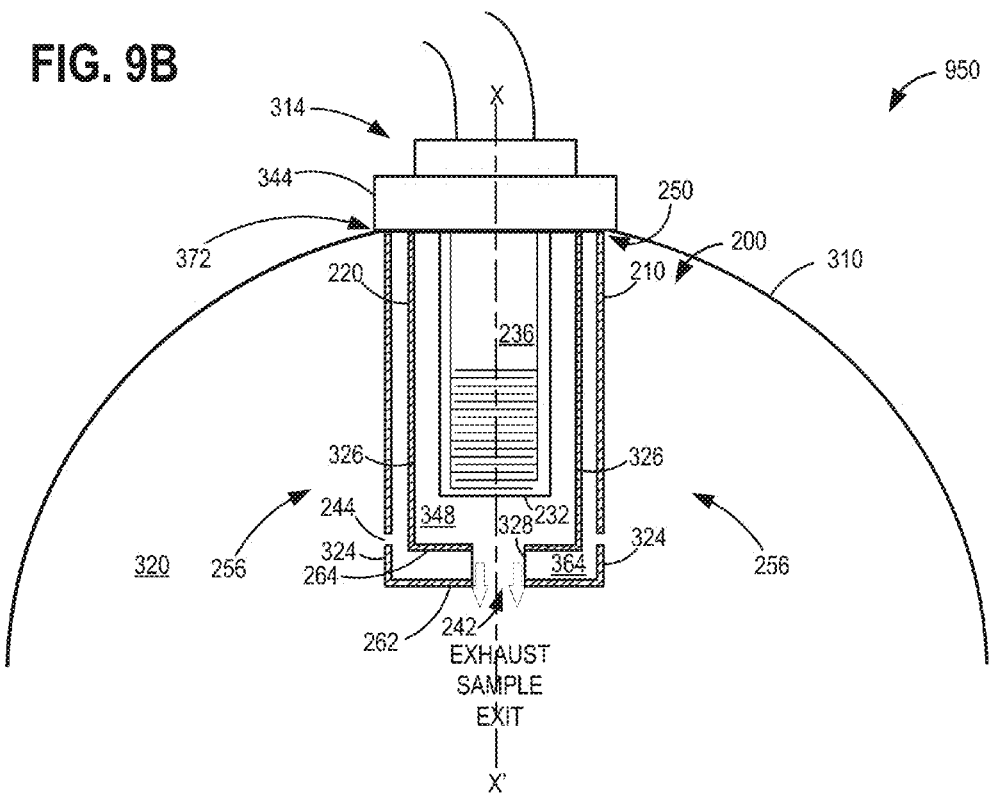

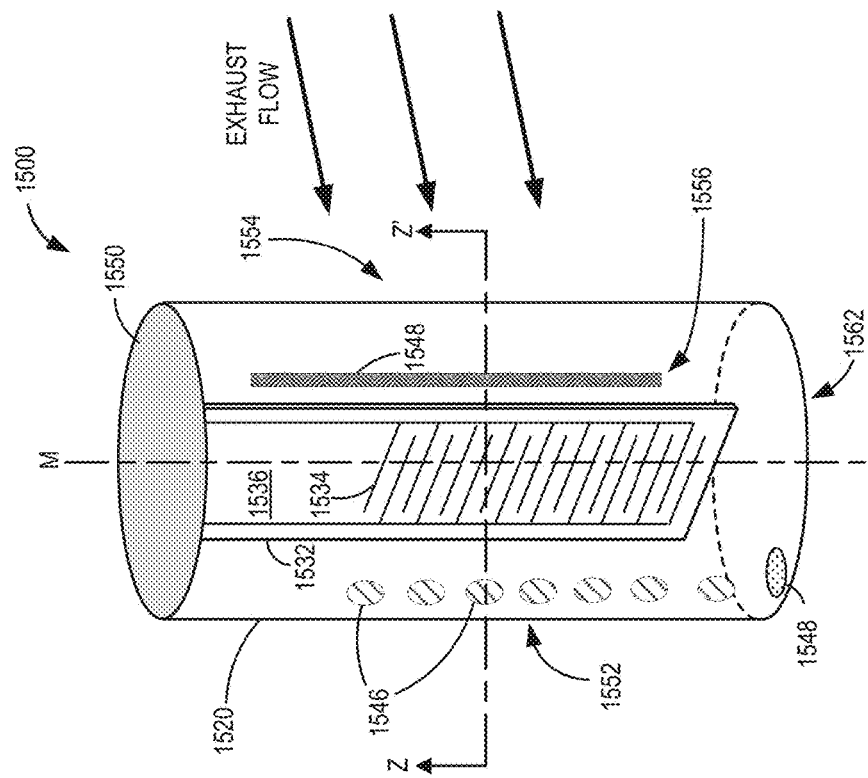
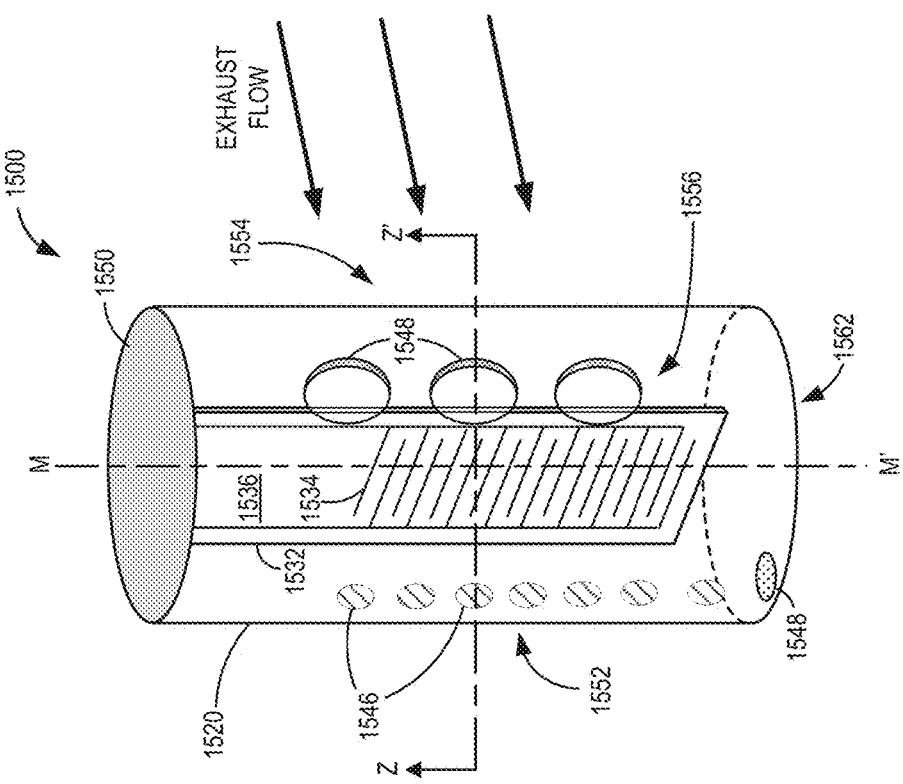

SYSTEM FOR SENSING PARTICULATE MATTER

CROSS REFERENCE TO RELATED APPLICATIONS

The present application is a continuation-in-part of U.S. patent application Ser. No. 14/299,885, "SYSTEM FOR SENSING PARTICULATE MATTER," filed on Jun. 9, 2014, the entire contents of which is incorporated herein by reference for all purposes. The present application also claims priority to U.S. Provisional Patent Application No. 62/077,140, "A PARTICULATE MATTER SENSOR," filed Nov. 7, 2014, the entire contents of which is incorporated herein by reference for all purposes.

TECHNICAL FIELD

The present application relates to sensing particulate matter in an exhaust system.

BACKGROUND AND SUMMARY

Engine emission control systems may utilize various exhaust sensors. One example sensor may be a particulate matter sensor which indicates particulate matter mass and/or concentration in the exhaust gas. In one example, the particulate matter sensor may operate by accumulating particulate matter over time and providing an indication of the degree of accumulation as a measure of exhaust particulate matter levels.

Particulate matter sensors may encounter problems with non-uniform deposition of soot on the sensor due to a bias in flow distribution across the surface of the sensor. Further, particulate matter sensors may be prone to contamination from an impingement of water droplets and/or larger particulates present in the exhaust gases. This contamination may lead to errors in sensor output. Furthermore, sensor regeneration may be inadequate when a substantial quantity of exhaust gases stream across the particulate matter sensor.

The inventors herein have recognized the above issues and identified an approach to at least partly address the issues. In one example approach, a system for sensing particulate matter in an exhaust passage of an engine is provided. The system comprises a first outer tube with a plurality of intake apertures on an upstream surface, a second inner tube with a plurality of intake apertures on a downstream surface, and a particulate matter sensor placed within the second inner tube.

For example, a particulate matter (PM) sensor may be disposed within a second inner tube, the second inner tube being enclosed within a first outer tube. The first outer tube may have a plurality of perforations on an upstream surface of the first outer tube facing an oncoming exhaust flow. Further, the second inner tube may have a group of perforations distributed on a downstream surface of the second inner tube, the downstream surface facing away from exhaust flow. The PM sensor may include an electrical circuit on one of its surfaces, and the PM sensor may be positioned within the inner tube such that the surface with the electric circuit faces the intake perforations on the downstream surface of the second inner tube. Accordingly, a sample of exhaust gases may enter the first outer tube via the upstream perforations, flow around an annular space between the second inner tube and the first outer tube, and enter the second inner tube via the group of perforations on the downstream surface of the inner tube. The sample of exhaust gases may then impinge on and flow across the surface of the PM sensor with the electrical circuit. Finally, the sample of exhaust gases may exit the second inner tube via channels that fluidically connect the second inner tube with the exhaust passage.

In this way, a PM sensor may be exposed to a more uniform flow distribution across its surface. By guiding the sample of exhaust gases through two sets of apertures, the flow rate of the sample of exhaust gases may be controlled. Further, the flow rate may be more even as it impinges on the surface of the PM sensor allowing for a more uniform deposition of particulates. By providing a more even and controlled flow rate of the sample of exhaust gases onto the PM sensor surface, sensor regeneration may occur with reduced heat loss. Further, as the sample of exhaust gases is streamed through the annular space between the two protective tubes, larger particulates and/or water droplets may be deposited on the inner downstream surface of the first outer tube due to their larger momentum. Therefore, the PM sensor may be protected from impingement of water droplets and larger particulates. Overall, the functioning of the PM sensor may be improved and may be more reliable.

In another example, a PM sensor may be disposed within a single protection tube having a plurality of perforations on a downstream surface facing away from oncoming exhaust flow. Further, the protective tube may have one or more exit apertures positioned on side surfaces of the protective tube, where the side surfaces are tangential to the oncoming exhaust flow. Flowing exhaust gas around the protective tube, may create areas of lower pressure exterior to the side surfaces of the protective tube, relative to areas exterior to the downstream surface of the protective tube. Due to the pressure differential between the downstream and side surfaces of the protective tube, exhaust gas may naturally be drawn into the downstream perforations, onto the PM sensor, and then out of the protective tube through the exit channels on the side surfaces of the protective tube. Thus, the flow direction of a portion of exhaust gas flowing past the protective tube may be reversed, such that the portion of exhaust gas may flow towards the perforations on the downstream surface of the protective after having flowed past the protective tube.

In this way, a PM sensor may be exposed to a more uniform flow distribution across its surface. By guiding the sample of exhaust gases around the protective tube before entering the protective tube through the intake perforations on the downstream surface of the protective tube, the flow rate of the sample of exhaust gases may be controlled. Further, the flow rate may be more even as it impinges on the surface of the PM sensor allowing for a more uniform deposition of particulates. By providing a more even and controlled flow rate of the sample of exhaust gases onto the PM sensor surface, sensor regeneration may occur with reduced heat loss. Further, as the sample of exhaust gases is streamed from the downstream surface of the protective tube, the amount of larger particulates and/or water droplets impinging on the PM sensor may be reduced. Specifically, due to their larger momentum, water droplets and/or larger particulates may flow past the protective tube without redirecting their flow direction to enter the protective tube through the perforation on the downstream surface of the protective tube. Therefore, the PM sensor may be protected from impingement of water droplets and larger particulates. Overall, the functioning of the PM sensor may be improved and may be more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 7A-7B show schematic illustrations of two additional embodiments of the PM sensor assembly of FIGS. 2A-2B.

FIGS. 9A-9B depict a cross sectional views of the embodiments of the PM sensor assembly shown in FIGS. 7A-7B and FIGS. 8A-8B respectively.

FIGS. 15A-15B portray a schematic illustration of a PM sensor assembly comprising only one protection tube.

DETAILED DESCRIPTION

Figure 1:
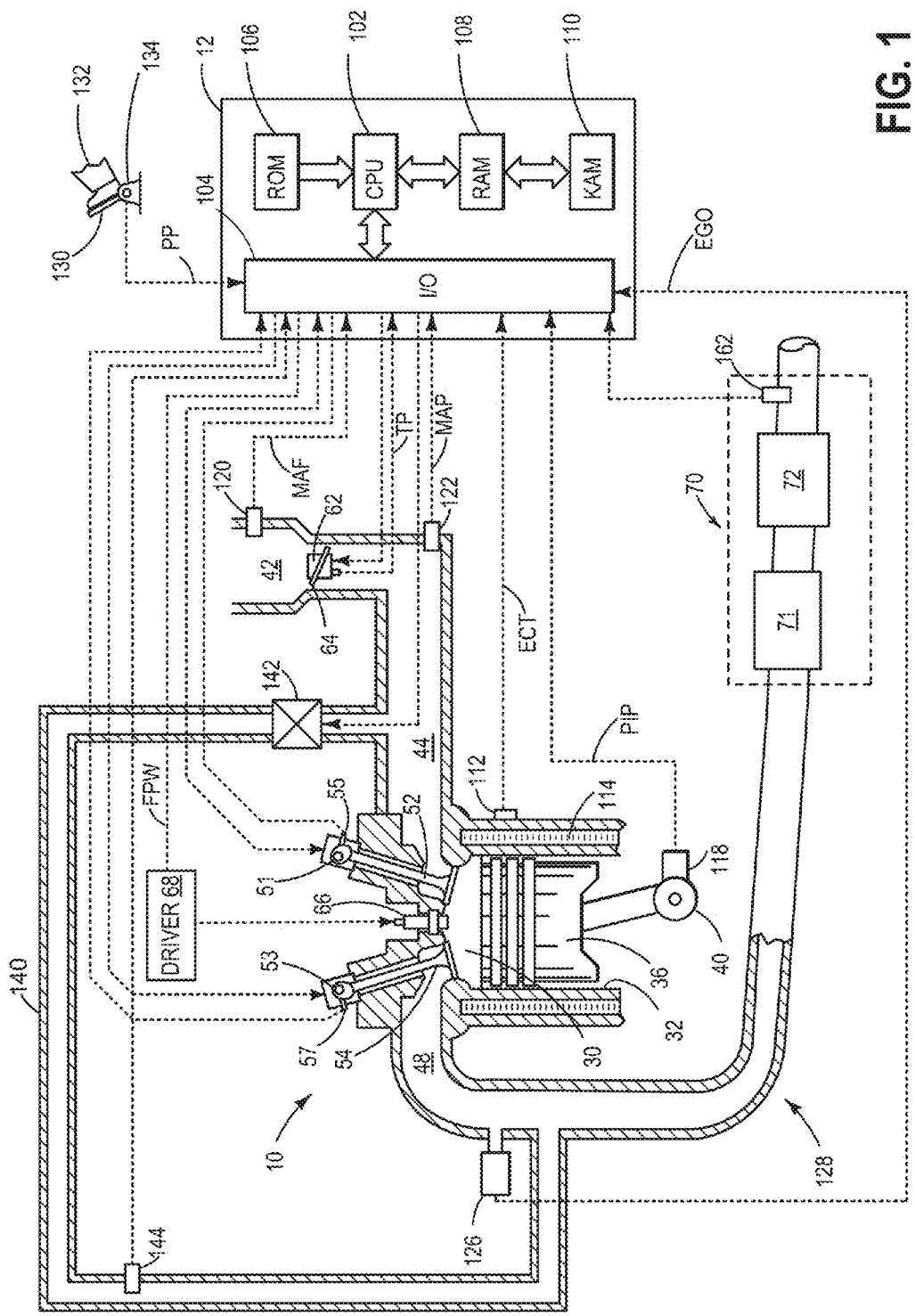
FIG. 1 is a schematic diagram of an engine.
Figure 5:
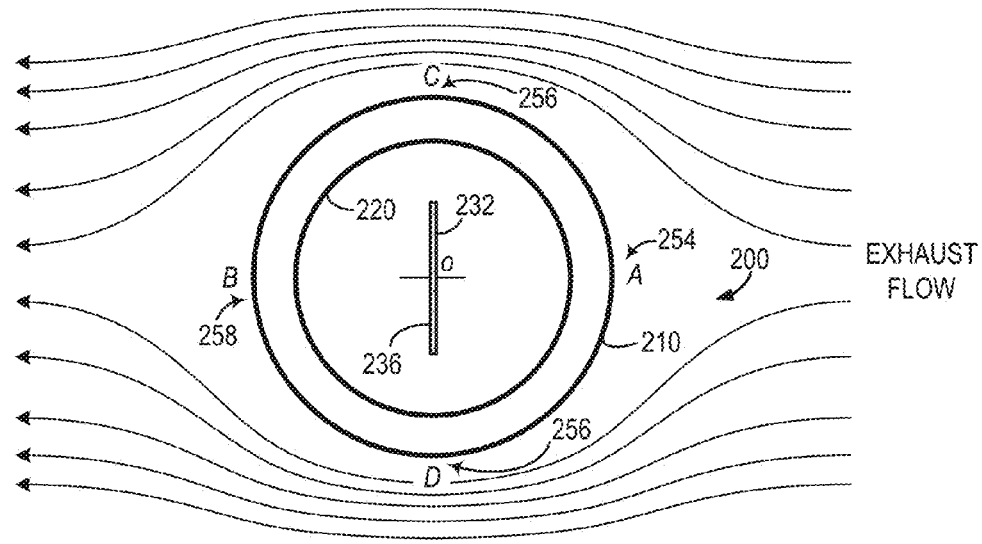
FIG. 5 is an example fluid flow around a cross-section of the PM sensor assembly.
Figure 6:
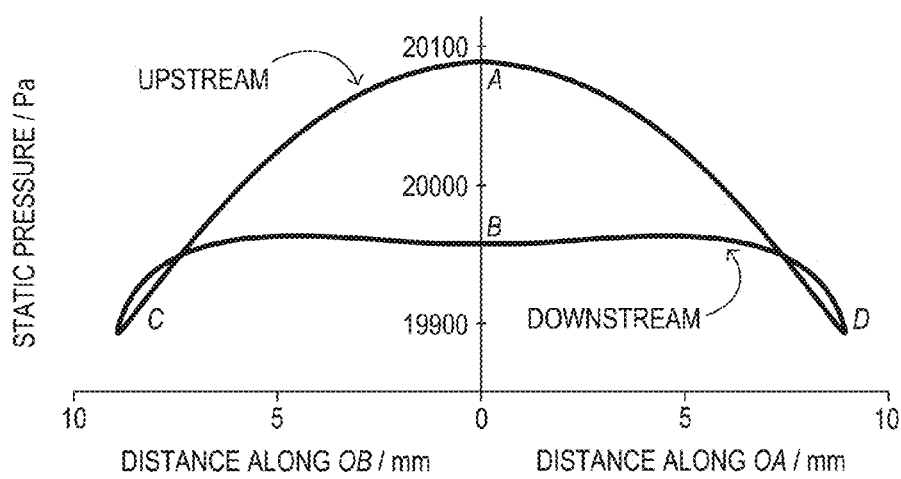
FIG. 6 is a graphical depiction of an example fluid-dynamics calculation in accordance with the structure illustrated in FIG. 5.
Figure 8A:
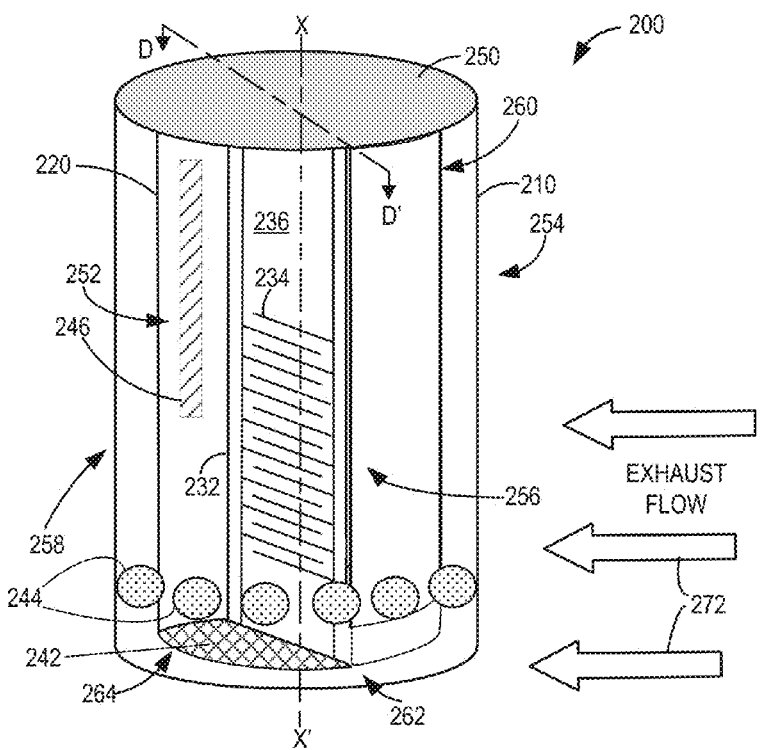
FIGS. 8A-8B show schematic illustrations of two additional embodiments of the PM sensor assembly of FIGS. 2A-2B.
Figure 8B:
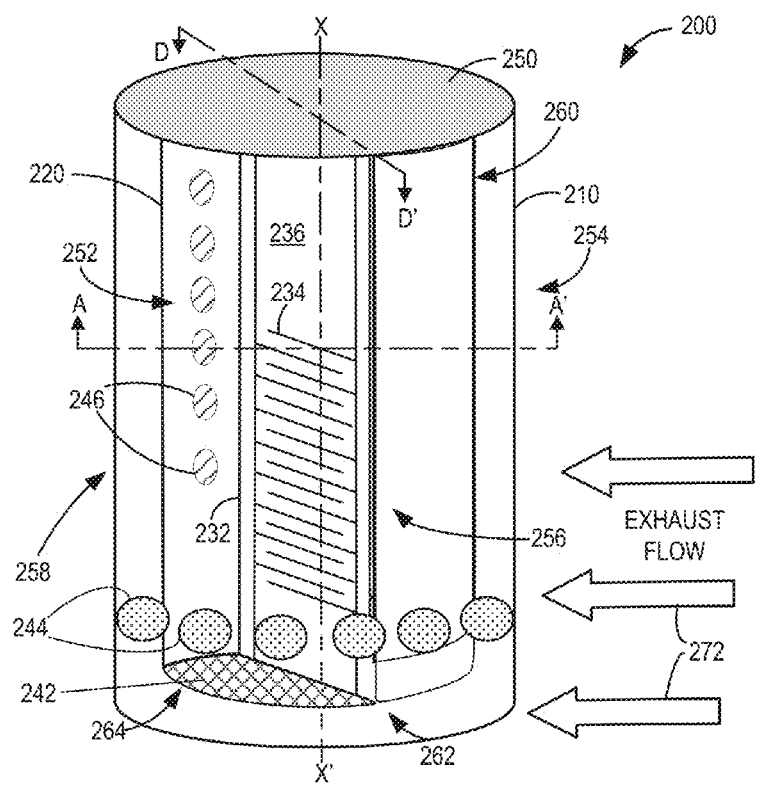
Figure 17:
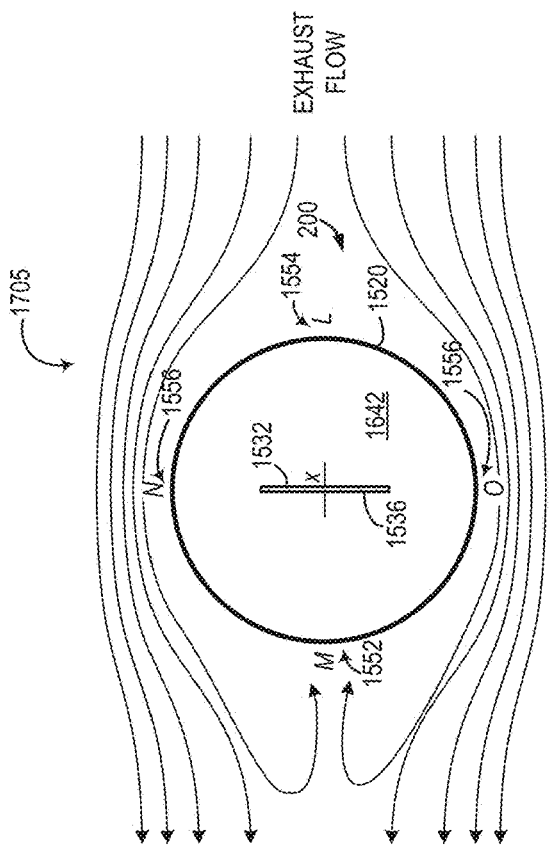
FIG. 17 is an example fluid flow around a cross-section of the PM sensor assembly shown in FIGS. 15A-15B.
Figure 16:
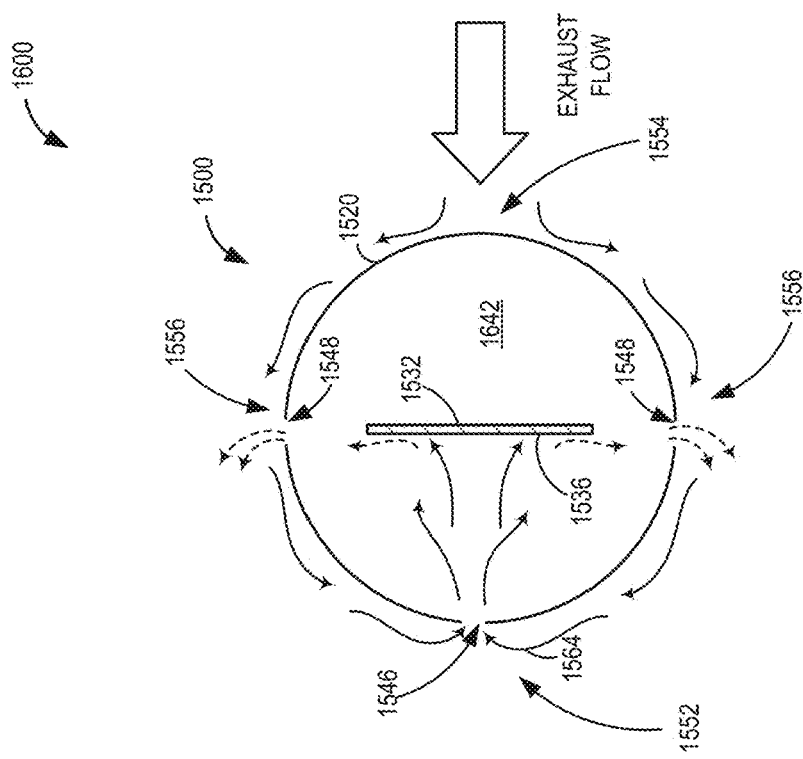
FIG. 16 is a cross sectional view of the PM sensor assembly shown in FIG. 15.
Figure 18:
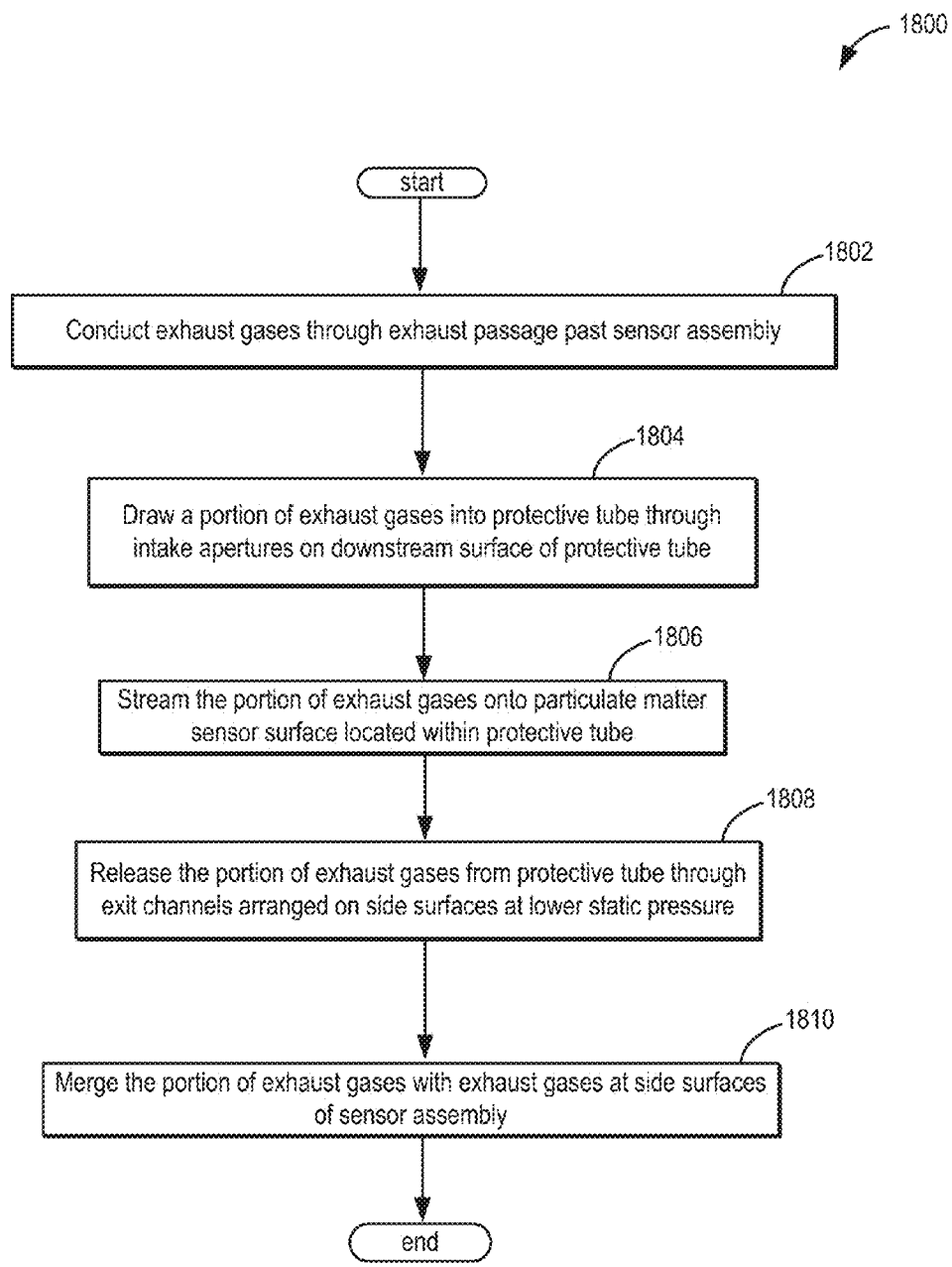
FIG. 18 is an example flowchart of a method for sensing PM using the PM sensor assembly shown in FIGS. 15A-15B.

The following description relates to sensing particulate matter (PM) in an exhaust flow of an engine system, such as the engine system shown in FIG. 1. A PM sensor may be placed in an exhaust passage of the engine system, as shown in FIG. 3 and FIG. 9. The PM sensor assembly may include a first outer tube with apertures on an upstream surface and a second inner tube with apertures on a downstream surface (FIGS. 2A, 2B and FIGS. 7A, 7B). Intake apertures may also be positioned around a circumference of the PM sensor near the base of the sensor (FIGS. 8A and 8B). The PM sensor may be enclosed within the second inner tube. A portion of exhaust gases may be drawn into the first outer tube of the PM sensor assembly whereupon the portion of gases may flow within an annular space between the first outer tube and the second inner tube and eventually enter the second inner tube (FIGS. 4A, 4B, 10 and FIG. 14). The portion of exhaust gases may then impinge on a surface of the PM sensor bearing an electrical circuit. Finally, the portion of exhaust gases may exit the inner tube via channels on either side surfaces or a bottom surface of the PM sensor assembly as shown in FIGS. 3, 4A, 4C, 9, and 10. Exhaust flow in the exhaust passage past the PM sensor assembly may create low static pressure zones at the side surfaces of the PM sensor assembly (FIGS. 5 and 6). The PM sensor assembly may be placed in a reversed orientation such that a sample of exhaust gas enters the first outer tube from apertures on a downstream surface, flows through an annular space between the first outer tube and the second inner tube, and enters the second inner tube from apertures on an upstream surface (FIGS. 8 and 9). The PM sensor may be positioned within the second inner tube such that the electrical circuit faces the upstream holes on the second inner tube allowing an impingement of exhaust gases onto the circuit so that feedback may be provided to a controller. Another embodiment of a PM sensor assembly may include a single protective tube around the PM sensor (FIGS. 15A, 15B). The protective tube may be placed in the exhaust passage such that intake apertures may be positioned on a surface of the tube facing downstream of the direction of gas flow in the exhaust passage. Exhaust flow in the exhaust passage past the PM sensor assembly may create low static pressure zones at the side surfaces of the PM sensor assembly (FIG. 17). Due to the pressure differential created by the exhaust gasses flowing around the protective tube, exhaust gas may enter the first outer tube through the apertures on the downstream surface of the tube, flow onto PM sensor, and exit the tube out from channels positioned on the side surfaces of the protective tube (FIG. 16). An example sensing operation of the PM sensor assembly with a single protective tube is shown in FIG. 18.

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber 30 (also termed, cylinder 30) of the engine 10 may include combustion chamber walls 32 with a piston 36 positioned therein. Piston 36 may be coupled to a crankshaft 40 so that reciprocating motion of the piston is translated into rotational motion of the crankshaft. Crankshaft 40 may be coupled to at least one drive wheel (not shown) of a vehicle via an intermediate transmission system (not shown). Further, a starter motor (not shown) may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled to the cylinder 30 for injecting fuel directly therein in proportion to the pulse width of signal FPW received from controller 12 via electronic driver 68. In this manner, fuel injector 66 provides what is known as direct injection of fuel into combustion chamber 30. It will also be appreciated that the cylinder 30 may receive fuel from a plurality of injections during a combustion cycle. In other examples, the fuel injector may be mounted in the side of the combustion chamber or in the top of the combustion chamber, for example. Fuel may be delivered to fuel injector 66 by a fuel system (not shown) including a fuel tank, a fuel pump, and a fuel rail.

In the example shown in FIG. 1, engine 10 is configured as a diesel engine that combusts air and diesel fuel through compression ignition. In other embodiments, the engine 10 may combust a different fuel including gasoline, biodiesel, or an alcohol containing fuel blend (e.g., gasoline and ethanol, or gasoline and methanol) through compression ignition and/or spark ignition. Thus, the embodiments described herein may be used in any suitable engine, including but not limited to, diesel and gasoline compression ignition engines, spark ignition engines, direct or port injection engines, etc.

The intake passage 42 may include a throttle 62 having a throttle plate 64. In this particular example, the position of the throttle plate 64 may be varied by controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by throttle position signal TP. The intake passage 42 may include a mass air flow sensor 120 and a manifold air pressure sensor 122 for providing respective signals MAF and MAP to the controller 12.

Further, in the disclosed embodiments, an exhaust gas recirculation (EGR) system may route a desired portion of exhaust gas from the exhaust passage 48 to the intake manifold 44 via an EGR passage 140. The amount of EGR provided may be varied by controller 12 via an EGR valve 142. By introducing exhaust gas to the engine 10, the amount of available oxygen for combustion is decreased, thereby reducing combustion flame temperatures and reducing the formation of $NO_x$, for example. As depicted, the EGR system further includes an EGR sensor 144 which may be arranged within the EGR passage 140 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 128 includes an exhaust gas sensor 126 coupled to the exhaust passage 48 upstream of an emission control system 70. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or CO sensor.

Emission control system 70 is shown arranged along exhaust passage 48 downstream of exhaust gas sensor 126. Emission control system 70 may be a selective catalytic reduction (SCR) system, three way catalyst (TWC), $NO_x$ trap, various other emission control devices, or combinations thereof. For example, emission control system 70 may include an SCR catalyst 71 and a diesel particulate filter (DPF) 72. In some embodiments, DPF 72 may be located downstream of the SCR catalyst 71 (as shown in FIG. 1), while in other embodiments, DPF 72 may be positioned upstream of the SCR catalyst 71 (not shown in FIG. 1). Emission control system 70 may further include exhaust gas sensor 162. Sensor 162 may be any suitable sensor for providing an indication of a concentration of exhaust gas constituents such as a $NO_x$, $NH_3$, EGO, or particulate matter (PM) sensor, for example. In some embodiments sensor 162 may be located downstream of DPF 72 (as shown in FIG. 1), while in other embodiments, sensor 162 may be positioned upstream of DPF 72 (not shown in FIG. 1). Further, it will be appreciated that more than one sensor 162 may be provided in any suitable position.

As described in more detail with reference to FIG. 2, sensor 162 may be a PM sensor and may measure the mass or concentration of particulate matter downstream of DPF 72. For example, sensor 162 may be a soot sensor. Sensor 162 may be operatively coupled to controller 12 and may communicate with controller 12 to indicate a concentration of particulate matter within exhaust exiting DPF 72 and flowing through exhaust passage 48. In this way, sensor 162 may detect leakages from DPF 72.

Further, in some embodiments, during operation of engine 10, emission control system 70 may be periodically reset by operating at least one cylinder of the engine within a particular air/fuel ratio.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; absolute manifold pressure signal, MAP, from the sensor 122; and exhaust constituent concentration from the exhaust gas sensor 126. Engine speed signal, RPM, may be generated by controller 12 from signal PIP.

As described above, FIG. 1 shows only one cylinder of a multi-cylinder engine, and each cylinder may similarly include its own set of intake/exhaust valves, fuel injector, spark plug, etc.

Figure 2A:
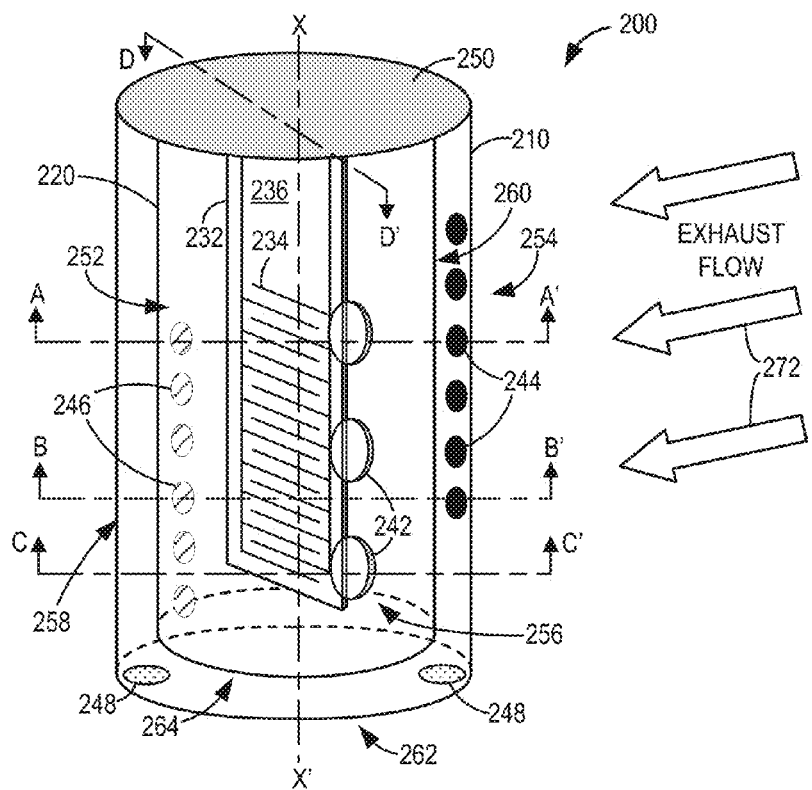
FIGS. 2A-2B show schematic illustrations of a particulate matter (PM) sensor assembly comprising two protection tubes, in accordance with the present disclosure.
Figure 2B:
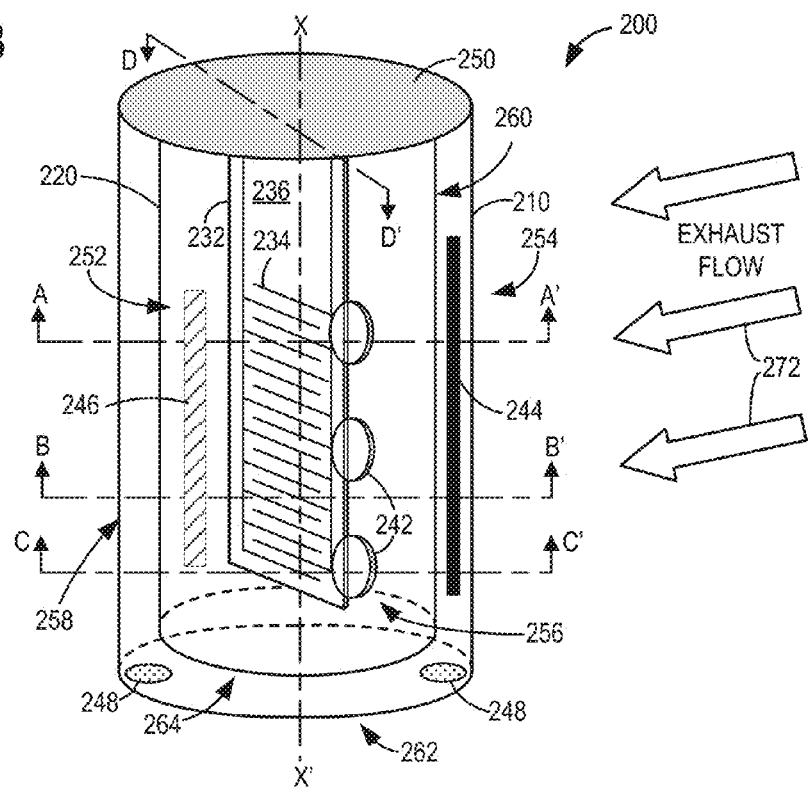
Figure 3:
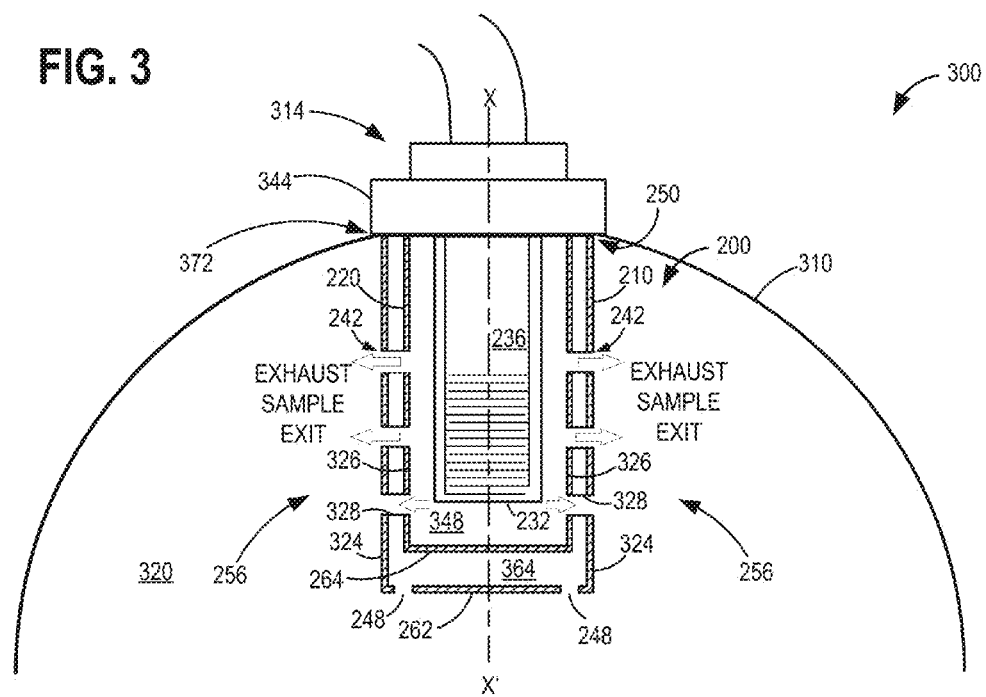
FIG. 3 shows a sectional view of the PM sensor assembly as placed in an exhaust passage of the engine of FIG. 1.

Turning now to FIGS. 2A-2B, a schematic view of two example embodiments of a PM sensor assembly 200 are shown. The only differences in the PM sensor assembly 200 shown in FIGS. 2A and 2B may be the apertures 244 and 246 (described in greater detail below); otherwise the PM sensor assembly 200 may be identical in FIGS. 2A and 2B. Thus, FIG. 2B is used to show how the shape and size of apertures 244 and 246 of the PM sensor assembly 200 may be variable. PM sensor assembly 200 may be exhaust gas sensor 162 of FIG. 1 and therefore may share common features and/or configurations as those already described for exhaust gas sensor 162. PM sensor assembly 200 may be configured to measure PM mass and/or concentration in the exhaust gas, and as such, may be coupled to an exhaust passage. It will be appreciated that PM sensor assembly 200 is shown in simplified form by way of example and that other configurations are possible.

PM sensor assembly 200 is shown from a downstream perspective inside exhaust passage 48 of FIG. 1 such that exhaust gases are flowing from the right hand side of FIGS. 2A-2B to the left hand side of FIGS. 2A-2B as indicated by arrows 272. PM sensor assembly 200 may include a first outer tube 210 with one or more apertures 244 (also termed perforations 244) distributed on an upstream surface 254 of first outer tube 210. Apertures 244 (or intake apertures 244) may serve as intake apertures for sampling exhaust gases for particulate matter. As shown in the example of FIG. 2A, intake apertures 244 may comprise a plurality of circular apertures aligned with one another along a vertical axis of the first outer tube 210 parallel to a central axis X-X' of the first outer tube 210. In other examples, as described below with reference to FIGS. 8A and 8B, the plurality of circular apertures which may comprise apertures 244 may extend around a circumference of the first outer tube 210. However in another embodiment, as shown in FIG. 2B, the one or more intake apertures 244 may be rectangular. Specifically, the intake apertures 244 may be rectangles with a first pair of parallel sides longer than a second pair of parallel sides. Further the rectangular intake apertures 244 may be positioned on the first outer tube 210, such that the first pair of parallel sides are parallel to the central axis X-X' of the first outer tube 210. In one example, the intake apertures 244 may comprise only one rectangular aperture as shown in FIG. 2B. However, in other examples, the intake apertures 244 may comprise more than one rectangular aperture. The intake apertures 244 may extend all the way from a bottom surface 262 to a top surface 250 of the PM sensor assembly 200. In other examples, as shown in FIGS. 2A-2B, the intake apertures may not extend from the bottom surface 262 to the top surface 250 and may be fully contained within an upstream surface 254 of the first outer tube 210. Upstream surface 254 of first outer tube 210 is substantially normal to and facing the flow of oncoming exhaust gases (arrows 272) in the exhaust passage 48 of FIG. 1. Thus, upstream surface 254 may be in direct contact with exhaust flow, and exhaust gases exiting DPF 72 may flow in an unobstructed manner towards upstream surface 254 of first outer tube 210 of PM sensor assembly 200. Further, no components may block or deflect the flow of exhaust gases from the DPF to PM sensor assembly 200. Thus, a portion of exhaust gases for sampling may be conducted via apertures 244 into PM sensor assembly 200. First outer tube 210 may not include any apertures on its downstream surface 258.

PM sensor assembly 200 further comprises a second inner tube 220 fully enclosed within first outer tube 210. Second inner tube 220 may be positioned such that a central axis of second inner tube is parallel to a central axis of first outer tube 210. In the example shown in FIG. 2, the central axis X-X' of second inner tube 220 coincides with, and may be the same as, corresponding central axis X-X' of first outer tube 210 resulting in a concentric arrangement of second inner tube within first outer tube. Therefore, an annular space (not shown in FIG. 2) may be formed between first outer tube 210 and second inner tube 220. Specifically, the annular space may be formed between an exterior surface of second inner tube 220 and an interior surface of first outer tube 210. In alternate embodiments, the central axis of first outer tube 210 may not coincide with, but may be parallel to, the central axis of second inner tube 220. However, an annular space between the first outer tube and the second inner tube may be maintained.

Second inner tube 220 also features apertures 246 (or intake apertures 246) on a downstream surface 252 of second inner tube 220. Apertures 246 may function as intake apertures for sampling a portion of exhaust gases drawn into first outer tube 210. Further, second inner tube may not include intake apertures on its upstream surface 260. Similarly to intake apertures 244, intake apertures 246 may be circular or rectangular. In the example shown in FIG. 2A, intake apertures 246 may comprise a plurality of circular apertures aligned with one another along a vertical axis of the second inner tube 220 parallel to a central axis (e.g., central axis X-X') of the second inner tube 220. However in another embodiment, as shown in FIG. 2B, the one or more intake apertures 246 may be rectangular. Specifically, the intake apertures 246 may be rectangles with a first pair of parallel sides longer than a second pair of parallel sides. Further the rectangular intake apertures 246 may be positioned on the second inner tube 220, such that the first pair of parallel sides are parallel to the central axis of the second inner tube 220. In the example shown in FIG. 2B, the intake apertures 246 may comprise only one rectangular aperture. However, in other examples, the intake apertures 246 may comprise more than one rectangular aperture. The intake apertures 246 may extend all the way from a bottom surface 264 of the second inner tube 220 to the top surface 250 of the PM sensor assembly 200. In other examples, as shown in FIGS. 2A-2B, the intake apertures may not extend from the bottom surface 264 to the top surface 250, and may be fully contained within a downstream surface 252 of the second inner tube 220. Downstream surface 252 of second inner tube 220 includes a surface substantially normal to exhaust flow and facing away from the flow of exhaust gases in the exhaust passage. Further, downstream surface 252 of second inner tube 220 is located within first outer tube 210 and therefore, is not in direct contact with exhaust flow in exhaust passage 48 of FIG. 1. However, downstream surface 252 may be in direct contact with the portion of exhaust gases conducted via apertures 244 of first outer tube 210. Therefore, the portion of exhaust gas conducted into PM sensor assembly 200 via apertures 244 of first outer tube 210 may be guided into an interior space (not shown) within second inner tube 220 via apertures 246 of second inner tube 220. Thus, second inner tube 220 may encompass a hollow interior space within.

PM sensor assembly 200 further includes a PM sensor 232 placed in the interior space within second inner tube 220. Therefore, PM sensor 232 may be completely enclosed within second inner tube 220, which in turn may be surrounded by first outer tube 210. First outer tube and second inner tube may, thus, may serve as shields or protection for PM sensor.

PM sensor 232 may include an electrical circuit 234 located on a first surface 236. Further, PM sensor 232 may be placed within second inner tube 220 such that first surface 236 faces the plurality of apertures 246 on downstream surface 252 of second inner tube 220. Therefore, the portion of exhaust gases guided into the interior, hollow space within second inner tube 220 may impinge onto first surface 236 of PM sensor 232. Particulate deposition from the portion of exhaust gases onto first surface 236 may create a bridge or shortcut within the electrical circuit 234 and alter an output, e.g., current or voltage, of PM sensor 232. The output from PM sensor 232 may, therefore, be an indication of the cumulative particulate matter in the samples of exhaust that the sensor measures.

Second inner tube 220 may be fluidically coupled to the exhaust passage via one or more channels 242 which in the examples shown in FIGS. 2A and 2B, may be located on side surfaces 256 of PM sensor assembly. Side surfaces 256 may be substantially tangential to a direction of exhaust flow in the exhaust passage. Further, channels 242 fluidically couple only the interior space within second inner tube 220 to the exhaust passage allowing the portion of exhaust gases within the second inner tube 220 alone to exit the PM sensor assembly 200. Channels 242 may be formed as walled passages wherein the walls block access to the annular space between first outer tube 210 and second inner tube 220. Therefore, channels 242 may be sealed off from first outer tube 210. Accordingly, the portion of exhaust gases drawn into the first outer tube 210 may flow into the second inner tube 220 alone, and may not exit the PM sensor assembly directly from the first outer tube 210. Thus, the portion of exhaust gases within the hollow, interior space of second inner tube 220 may exit via one or more channels 242 arranged on side surfaces 256 of PM sensor assembly. In the examples shown in FIGS. 2A-2B, the one or more exit channels 242 may be circular and may be aligned along the side surfaces 256 along an axis parallel the central axis X-X' of the first outer tube 210. However in other examples, the one or more exit channels 242 may be rectangular. In still further examples, as will be described in greater detail below with reference to FIGS. 7A, 7B, 8A, and 8B, the one or more exit channels 242 may originate at the bottom surface 264 of the second inner tube 220, and may allow exhaust gas to exit out the bottom of the PM sensor assembly 200 through the bottom surface 262 of the first outer tube 210.

In the example of FIGS. 2A and 2B, each of the first outer tube 210 and the second inner tube 220 may have circular cross-sections. In alternative embodiments, different cross-sections may be used. In one example, the first outer tube 210 and second inner tube 220 may be hollow tubes formed from metal capable of withstanding higher temperatures in the exhaust passage. In another example, alternative materials may be used. Further still, each of the first outer tube and second inner tube may be formed from distinct materials. In addition, material selected for manufacturing the first outer tube and the second inner tube may be such that can tolerate exposure to water droplets released from the DPF.

PM sensor assembly 200 may be coupled to exhaust passage 48 (FIG. 1) in a suitable manner such that the top surface 250 of PM sensor assembly is sealed to a wall of the exhaust passage. The coupling of the PM sensor assembly 200 to the wall of the exhaust passage will be elaborated below in reference to FIG. 3.

First outer tube 210 may include one or more drainage holes 248 dispersed on bottom surface 262 to allow water droplets and larger particulates to drain from PM sensor assembly 200. The size, number, and location of drainage holes 248 may be based on design parameters of the PM sensor assembly. In the example of PM sensor assembly 200, two drainage holes 248 are depicted. In alternate embodiments, the number of drainage holes may be higher or fewer. Further, their size and location may be different from that depicted in the given example.

Second inner tube 220 may be completely sealed and closed at bottom surface 264. The sealing of second inner tube 220 at bottom surface 264 may be accomplished during production of PM sensor assembly 200. Further, the closure of bottom surface 264 may ensure that the portion of exhaust gases within the second inner tube 220 exits solely via channels 242. Additional details regarding PM sensor assembly 200 will be elaborated in reference to FIGS. 3-4 below.

PM sensor assembly 200 may be positioned within exhaust passage 48 and configured to sample exhaust gases flowing within. A portion of exhaust gases may flow into PM sensor assembly 200 and first outer tube 210 via apertures 244 on the upstream surface 254 of first outer tube 210. The portion of exhaust gases may impinge on an exterior of the upstream surface 260 of the second inner tube 220 before circulating through an annular space formed between first outer tube 210 and second inner tube 220. The portion of exhaust gases may then enter the second inner tube 220 via apertures 246 on the downstream surface 252 of second inner tube 220 and may impinge on the first surface 236 of PM sensor 232. Finally, the portion of exhaust gases may exit the second inner tube 220 (and PM sensor assembly) via channels 242 and merge with rest of the exhaust flow in exhaust passage 48.

PM sensor 232 may be coupled to a heater (not shown) to burn off accumulated particulates, e.g. soot, and thus, may be regenerated. In this way, the PM sensor may be returned to a condition more suitable for relaying accurate information pertaining to the exhaust. Such information may include diagnostics that relate to the state of the DPF, and thus may at least in part determine if DPF leakage is present.

Turning now to FIG. 3, it schematically shows a longitudinal sectional view 300 of PM sensor assembly 200 in a longitudinal plane along line D-D' of FIG. 2. In the depicted example, PM sensor assembly 200 is coupled within exhaust pipe 310 (or conduit 310) and exhaust gases flow within area 320. Exhaust pipe 310 may be a portion of exhaust passage 48 in FIG. 1. Further, in the portrayed example of FIG. 3, exhaust gases are flowing towards the viewer within area 320. As such, the viewer is positioned downstream from PM sensor assembly 200 and is looking towards an upstream direction. Components previously introduced in FIGS. 1, 2A, and 2B are numbered similarly in FIGS. 3-4 and not reintroduced.

In the sectional view 300 depicted in FIG. 3, PM sensor assembly 200 is shown extending radially into exhaust pipe 310 and is coupled to a roof of exhaust pipe 310 (with respect to vertical). For example, PM sensor assembly 200 may be inserted through a central hole (not shown) in a boss 344 and coupled to exhaust pipe 310. Herein, boss 344 may be welded and joined to exhaust pipe 310 at an outer edge 372. In other examples, boss 344 may be joined to exhaust pipe 310 via alternative joining methods such as brazing, adhesion, etc., and may also be joined at different locations including outer edge 372.

In the example shown, PM sensor assembly 200 may be screwed into boss 344. For example, inner threads on an inner surface of central hole in boss 344 may engage with outer threads on a part of connector assembly 314 coupled to PM sensor assembly 200. Alternatively, other fastening methods may be used to couple PM sensor assembly 200 to boss 344, and therefore, to exhaust pipe 310. By inserting and attaching PM sensor assembly 200 to boss 344, and therefore, to exhaust pipe 310, a sealed joint may be formed between top surface 250 of PM sensor assembly 200 and exhaust pipe 310 via boss 344 to ensure an absence of leaks. Thus, exhaust gases flowing past PM sensor assembly 200 in exhaust pipe 310 may not escape into the atmosphere through the sealed joint.

In other examples, PM sensor assembly 200 may be located in alternate positions along the exhaust pipe 310. Further, PM sensor assembly 200 may be coupled to connector assembly 314 which may be operatively coupled to the controller.

As described earlier in reference to FIGS. 2A and 2B, second inner tube 220 may be fully enclosed within first outer tube 210. Annular space 364 may be formed between the first outer tube and the second inner tube. PM sensor 232 may be located within second inner tube 220 such that the first surface 236 with electrical circuit 234 faces the downstream direction (and the viewer). Second inner tube 220 may be sealed across its bottom surface 264 (with respect to vertical) such that there are no openings on bottom surface 264. In contrast, first outer tube 210 may include one or more drainage holes 248 at its bottom surface 262 (with respect to vertical) to allow the removal of water droplets and larger particulates that may be present within annular space 364 between first outer tube 210 and second inner tube 220.

FIG. 3 also depicts channels 242 that fluidically couple interior space 348 of second inner tube 220 with area 320 within exhaust pipe 310. Channels 242 may originate from side surfaces 326 of the second inner tube 220 and allow exhaust gases within interior space 348 to exit PM sensor assembly 200. Further, channels 242 may end on side surfaces 324 of first outer tube 210 of PM sensor assembly 200. Side surfaces 256 of PM sensor assembly 200, which includes side surfaces 324 of first outer tube, are substantially tangential to a direction of exhaust flow in the exhaust pipe 310. Further, side surfaces 324 of first outer tube 210 may be in direct contact with exhaust gases flowing in exhaust pipe 310.

It will be appreciated that the sizes (e.g., diameter) of plurality of apertures 244 distributed on upstream surface 254 of first outer tube, and sizes of the plurality of apertures 246 on downstream surface 252 of second inner tube may be optimized by using a model, such as a computational fluid dynamics (CFD) tool, for enabling a suitable gas flow rate into the PM sensor assembly 200. The model may also optimize the sizes of the apertures 244 and 246 to improve flow uniformity. By optimizing the apertures, a satisfactory sampling of exhaust gases may occur with an improvement in uniformity of flow, enabling a more uniform deposition of particulate matter on PM sensor first surface 236.

In the given example, each group of apertures, that is, 244 and 246, includes six apertures, as shown in FIG. 2. However, in alternate embodiments, each group or cluster of apertures may include a larger or smaller number of apertures. Similarly, channels 242 on side surfaces 256 include three channels on each side surface in the example of FIG. 3. In alternate embodiments, each group of channels may include a larger or smaller number of channels. The number of apertures and channels may also be based on the dimensions of the first outer tube 210 and the second inner tube 220.

Figure 4A:
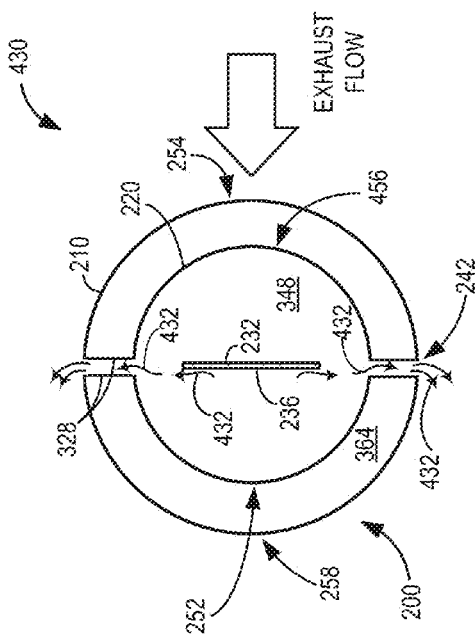
FIGS. 4A, 4B, and 4C depict multiple cross sectional views of the PM sensor assembly.
Figure 4B:
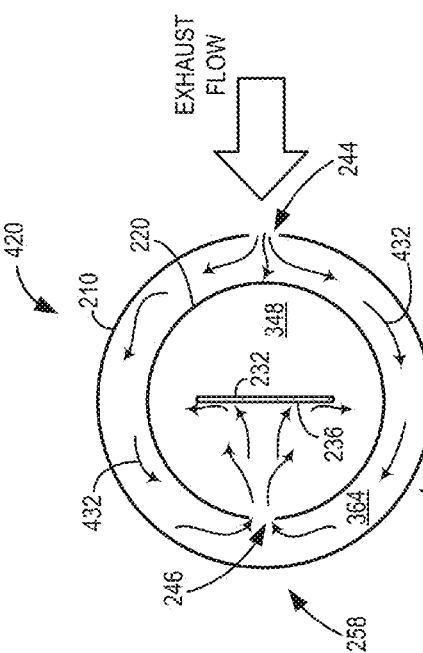
Figure 4C:
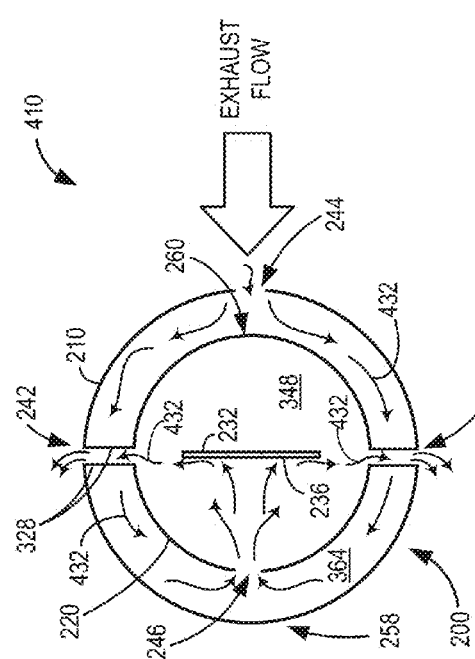

FIGS. 4A, 4B, and 4C schematically show cross sectional views of PM sensor assembly 200 along planes, A-A', B-B', and C-C', respectively. As such, components previously introduced in FIGS. 2 and 3 are similarly numbered and not reintroduced.

Referring to FIG. 4A, it shows a cross sectional view 410 along plane A-A' of FIG. 2 wherein the view (410) includes a section across PM sensor assembly with one or more upstream intake apertures 244 facing oncoming exhaust flow, one or more downstream intake apertures 246 on second inner tube, and channels 242. An example sampling method via PM sensor assembly 200 will be elaborated in detail below in reference to FIGS. 2, 3, and 4A.

As exhaust gases flow from right hand side to left hand side of FIG. 4A, a portion of exhaust gases 432 may enter PM sensor assembly 200 via the one or more intake apertures 244 at upstream surface 254 of first outer tube 210. The portion of exhaust gases 432 may strike the exterior of the upstream surface 260 of second inner tube 220 before being transported through annular space 364, formed between an interior surface of first outer tube 210 and an exterior surface of second inner tube 220. Thus, second inner tube 220 may act as an insulation shield for PM sensor 232 reducing heat loss from PM sensor 232 during regeneration. The portion of exhaust gases 432 may be streamed towards the downstream end of annular space 364. Herein, even though channels 242 appear to be blocking the passage of the portion of exhaust gases 432, the portion of exhaust gases 432 may flow either over or under channel 242 within annular space 364.

The portion of exhaust gases 432 may comprise water droplets, e.g., from the DPF, and larger particulates along with other dispersed constituents. In one example, these water droplets and larger particulates may be deposited on upstream surface 260 of second inner tube 220 upon impingement of the portion of exhaust gases 432. Herein, the deposited water droplets and larger particulates may sink to the bottom surface of first outer tube 210 and drain out through drainage holes 248. In another example, the water droplets and larger particulates may be transported through annular space 364.

The portion of exhaust gases 432 may then enter interior space 348 within second inner tube 220 via the one or more intake apertures 246 on downstream surface of second inner tube 220. Herein, the portion of exhaust gases 432 changes direction of flow by 180 degrees to enter second inner tube 220 from annular space 364. In this example, water droplets and larger particulates may not be able to change their flow direction due to their higher momentum and may be deposited on an interior downstream surface of first outer tube 210. These particulates and droplets may eventually gravitate towards bottom surface 262 of first outer tube 210 and may drain out of drainage holes 248.

As the portion of exhaust gases 432 enters second inner tube 220 via intake apertures 246, the exhaust gases may impinge on first surface 236 of PM sensor 232. By impinging the exhaust gases onto the surface of the PM sensor, instead of flowing exhaust gas samples across the surface of the PM sensor, uniformity of PM deposition may be enhanced. As described earlier in reference to FIG. 2, first surface 236 may feature electrical circuit 234 so that particulates, such as soot, may be deposited on first surface 236 and may be detected via electrical circuit 234. The portion of exhaust gases 432 may then exit interior space 348 of second inner tube 220, and therefore, the PM sensor assembly 200 via channels 242.

Thus, when the portion of exhaust gases 432 enters PM sensor assembly 200, it may flow first into the first outer tube 210, next into second inner tube 220, and subsequently exit the PM sensor assembly via channels 242. The portion of exhaust gases 432 may, therefore, not enter the second inner tube 220 directly. Further, the portion of exhaust gases 432 may not exit from the first outer tube 210 other than by flowing through second inner tube 220. Intake apertures 244 fluidically couple the exhaust passage to the annular space 364 within first outer tube 210, and intake apertures 246 fluidically couple annular space 364 to interior space 348 within second inner tube 220. Further, channels 242 fluidically couple interior space 348 within second inner tube 220 to the exhaust passage.

Even though first outer tube 210 includes drainage holes 248, the bulk portion of exhaust gases 432 may flow from annular space 364 within first outer tube 210 into interior space 348 of second inner tube 220 because of momentum and static pressure.

It will be appreciated that the portion of exhaust gases 432 may undergo three changes in flow direction: a first change in direction as the portion of exhaust gases enter the first outer tube 210 and turn to flow around annular space 364, a second change in direction as the portion of exhaust gases 432 enters second inner tube 220 from apertures 246, and a third change in direction as the portion of exhaust gases 432 impinges upon PM sensor and turns to exit the PM sensor assembly. These changes in flow direction may improve evenness of flow and also reduce flow rate within the PM sensor assembly.

Referring now to FIG. 4B, it shows a cross sectional view 420 along plane B-B' of FIG. 2 wherein the plane includes a section across PM sensor assembly with an upstream aperture 244 facing exhaust flow and a downstream aperture 246 on second inner tube. Cross sectional view 420 does not include channels 242. Herein, the portion of exhaust gases 432 drawn into first outer tube 210 flows in an unimpeded manner, relative to cross sectional view 410, through annular space 364.

FIG. 4C depicts a cross sectional view 430 along plane C-C' of FIG. 2 wherein the cross sectional view 430 features a section across PM sensor assembly including channels 242 but not including apertures 244 or 246.

The portion of exhaust gases 432 within interior space 348 may exit second inner tube 220 via channels 242 and merge with rest of exhaust flow surrounding PM sensor assembly 200. Channels 242 are shown fluidically connecting interior space 348 of second inner tube 220 with the exhaust passage. Further, channels 242 do not fluidically connect annular space 364 with the exhaust passage and may be separated from annular space 364 by channel walls 328. Therefore, exhaust gases within annular space 364 may be blocked from channels 242 and may not exit annular space 364 via channels 242. Exhaust gases within annular space 364 may exit the annular space 364 via downstream apertures 246 on second inner tube 220.

Channels 242 may be formed from the same material as the first outer tube and second inner tube. In other examples, channels 242 may be made from a different material based on ease of production and functionality. Further still, each of the first outer tube 210, the second inner tube 220, and channels 242 may be made of different materials. Channels 242 may be joined to first outer tube and second inner tube via joining methods such as welding, soldering, adhesion, etc. In one example, each channel may be formed as a hollow cylinder without end caps. As such, the cylindrical channel may include a curved wall without end surfaces. Further, the first outer tube and the second inner tube may have bores or apertures drilled through their side surfaces (324, 326) to accommodate the channels. The bores may be sized to form a close fit around the channels. Additionally, the bores of the first outer tube and second inner tube may be positioned to align with each other. For example, a first bore on a side surface of first outer tube may be located such that it aligns with a second bore drilled through a side surface of second inner tube. Finally, each channel may be fitted through a pair of bores and joined at its ends to the bores. Specifically, a channel may be inserted at a first end into the first bore on a side surface of first outer tube and a second end of the channel may be inserted into the second bore on the side surface of the second inner tube. Further, the first end and the second end of the channel may be joined to the first and second bores on the first outer tube and second inner tube, respectively. In this way, a fluidic coupling may be formed between an interior space enclosed within second inner tube and exhaust passage. Further, the first outer tube may not be fluidically coupled via the channels to the exhaust passage.

Thus, one embodiment of a particulate matter (PM) sensor assembly is introduced herein featuring a first outer tube with a plurality of gas intake apertures on an upstream surface, a second inner tube with a plurality of gas intake apertures on a downstream surface, and a particulate matter sensor placed within the second inner tube. The upstream surface may be a surface normal to and facing a flow of exhaust gases in the exhaust passage, and the downstream surface may be a surface facing away from the flow of exhaust gases in the exhaust passage.

Further, the second inner tube may be arranged within the first outer tube such that a central axis of the second inner tube is parallel to a central axis of the first outer tube. Further still, each of the first outer tube and the second inner tube may be sealed at the top with respect to vertical when coupled in an exhaust system of a vehicle traveling on a road. The first outer tube may also include a plurality of drainage holes at a bottom surface with respect to vertical. Additionally, a bottom surface of the second inner tube with respect to vertical may be sealed. The particulate matter sensor within the second inner tube may incorporate an electrical circuit on a first surface and may be placed within the second inner tube such that the first surface with the electrical circuit faces the downstream surface of the second inner tube.

Turning now to FIG. 5, fluid (e.g., exhaust gas) flow around PM sensor assembly 200 is shown. The location marked "A" corresponds to upstream surface 254 of first outer tube 210, the location marked "B" corresponds to downstream surface 258 of first outer tube 210, and locations marked "C" and "D" correspond to side surfaces 324 of first outer tube 210 of PM sensor assembly 200.

FIG. 6 graphically illustrates a result of a fluid dynamics calculation based on the structure of FIG. 5. This result depicts that gas flow around PM sensor assembly 200 and specifically, first outer tube 210, causes a static pressure variation along the exterior of the sensor assembly. Further, FIG. 6 shows that a higher static pressure may exist at upstream location while a lower static pressure may exist at each of exterior side surfaces C and D. Further, static pressure at location B may be higher than that at side surfaces C and D but lower than static pressure at location A. In other words, positioning intake apertures at location A (and to a smaller extent, location B) and exit channels at side surfaces C and D may be more advantageous for sampling exhaust gases. The low static pressure at side surfaces naturally draws out exhaust gases from within PM sensor assembly while the higher static pressure at location A (and to a smaller extent, location B) may enable an easier drawing in of exhaust gases into PM sensor assembly. In the embodiments described herein, intake apertures and exit channels may be positioned to take advantage of this effect.

Turning now to FIGS. 7A and 7B, they portray alternative embodiments of the PM sensor assembly 200 of FIGS. 2-6. The embodiments of PM sensor assembly 200 presented in FIGS. 7A and 7B herein may be the same as the embodiments of PM sensor assembly 200 presented in FIGS. 2A and 2B, respectively, except that the exit channels 242 map be positioned at the bottom of the PM sensor assembly 200 instead of at side surfaces 256. Said another way, the only difference between the embodiments of the PM sensor assembly 200 in FIGS. 7A and 7B and FIGS. 2-6 may be the positioning of the exit channels 242 on the PM sensor assembly 200. As such, components of PM sensor assembly 200 already described in FIGS. 2-6 may not be described again in the description of FIGS. 7A and 7B herein. Further, the shape, orientation, and position of the intake apertures 244 and 246 shown in FIG. 7A may be the same as that in FIG. 2A. Thus, the intake apertures 244 shown in FIG. 7A may be circular, positioned on an upstream surface of the first outer tube 210, and be aligned along a central axis X-X' of the first outer tube 210. Similarly, the intake apertures 246 may be circular, positioned on a downstream surface of the second inner tube 220 and be aligned along a central axis (e.g., X-X') of the second inner tube 220. Further, the shape, orientation, and position of the intake apertures 244 and 246 shown in FIG. 7B may be the same as that in FIG. 2B. Thus, the intake apertures 244 shown in FIG. 7B may be rectangular, positioned on an upstream surface the first outer tube 210, and oriented such that a longer first pair of parallel sides of the apertures are parallel to a central axis of the first outer tube 210. Similarly, the intake apertures 246 in FIG. 7B may be rectangular, positioned on a downstream surface of the second inner tube 220, and oriented such that a longer first pair of parallel sides of the apertures are parallel to a central axis of the second inner tube 220.

In the embodiment of PM sensor assembly 200 shown in FIGS. 7A and 7B, the one or more exit channels may fluidically couple the interior of second inner tube 220 to the exterior of the PM sensor assembly 200. Channels 242 may originate from bottom surface 264 of the second inner tube 220 and allow exhaust gases within an interior space of the second inner tube 220 to exit PM sensor assembly 200. Further, channels 242 may end on bottom surface 262 of first outer tube 210 of PM sensor assembly 200. Bottom surface 262 is substantially parallel to a direction of exhaust flow exterior to the PM sensor assembly 200. Channels 242 may be sealed from the annular space that exists between the first outer tube 210 and the second inner tube 220. As such, the channels 242 may block exhaust gas in the annular space between first outer tube 210 and second inner tube 200 from exiting the PM sensor assembly without first passing through intake apertures 246 on the second inner tube 220. Thus channels 242 may ensure, that exhaust gas may only exit the PM sensor assembly 200 from within the second inner tube 220.

Thus, the embodiment of PM sensor assembly 200 shown in FIGS. 7A and 7B may be the same as shown in FIGS. 2A and 2B in that it may be positioned within exhaust passage 48 and configured to sample exhaust gases flowing within. A portion of exhaust gases may flow into PM sensor assembly 200 and first outer tube 210 via apertures 244 on the upstream surface 254 of first outer tube 210. The portion of exhaust gases may impinge on an exterior of the upstream surface 260 of the second inner tube 220 before circulating through an annular space formed between first outer tube 210 and second inner tube 220. The portion of exhaust gases may then enter the second inner tube 220 via apertures 246 on the downstream surface 252 of second inner tube 220 and may impinge on the first surface 236 of PM sensor 232. However, the embodiments of the PM sensor assembly 200 shown in FIGS. 7A and 7B may differ from those shown in FIGS. 2A and 2B in that the portion of exhaust gases may exit the second inner tube 220 (and PM sensor assembly) via channels 242 on the bottom of the PM sensor assembly 200 instead of side surfaces.

Turning now to FIGS. 8A and 8B, they portray alternative embodiments of the PM sensor assembly 200 of FIGS. 7A and 7B. The embodiments of PM sensor assembly 200 presented in FIGS. 8A and 8B herein may be the same as the embodiments of PM sensor assembly 200 presented in FIGS. 7A and 7B, respectively, except that the intake apertures 244 may be positioned around a circumference of the PM sensor assembly 200, instead of along an axis parallel to the central axis X-X' of the first outer tube 210. Just as in FIGS. 7A and 7B, exit channels 242 may be positioned at the bottom of the PM sensor assembly 200 instead of at side surfaces 256. Said another way, the only difference between the embodiments of the PM sensor assembly 200 in FIGS. 8A and 8B and FIGS. 7A and 7B may be the positioning of the intake apertures 244 on the PM sensor assembly 200. As such, components of PM sensor assembly 200 already described in FIGS. 2-7 may not be described again in the description of FIGS. 8A and 8B herein.

Further, the shape, orientation, and position of the intake apertures 246 shown in FIG. 8A may be the same as that in FIGS. 2A and 7A. Thus as shown in FIG. 8A, the intake apertures 246 may be circular, positioned on the downstream surface 252 of the second inner tube 220 and be aligned along a central axis (e.g., X-X') of the second inner tube 220. Further, the shape, orientation, and position of the intake apertures 246 shown in FIG. 8B may be the same as that in FIGS. 2B and 7B. Thus, as shown in FIG. 8B, the intake apertures 246 in FIG. 8B may be rectangular, positioned on a downstream surface of the second inner tube 220, and oriented such that a longer first pair of parallel sides of the apertures are parallel to a central axis of the second inner tube 220. It is important to note that in other examples the intake apertures 246 may be positioned on the upstream surface 260, or side surfaces of the second inner tube 220.

In the example of PM sensor assembly 200 shown in FIGS. 8A and 8B, the intake apertures 244 may positioned around a circumference of the first outer tube 210. Specifically, the intake apertures 244 may be positioned near the base of the PM sensor assembly 200, more proximate the bottom surface 262 of the first outer tube 210 than the top surface 250 of the PM sensor assembly 200. Intake apertures 246 may be positioned above (with respect to vertical on the central axis X-X') the intake apertures. Thus, upon entering the annular space between the first outer tube 210 and the second inner tube 220 through intake apertures 244, exhaust gas may flow upwards before entering the second inner tube 220 through intake apertures 246. In this way, water droplets and larger particulates may not be able to change their flow direction due to their higher momentum and may exit the PM sensor assembly through one or more of the apertures 244 located on downstream surface 258 of first outer tube 210. As such the amount of water droplet and larger particulate impingement on the PM sensor 232 may be reduced. Thus, in the example of PM sensor assembly 200 shown in FIGS. 8A and 8B, drainage holes 248 may not be included in the PM sensor assembly 200, as the one or more apertures 244 positioned on the downstream surface 258 near the bottom surface 262 may serve as drainage for water droplets and larger particulates. As such, the position of the intake apertures 244 around the circumference of the first outer tube 210 may serve a dual function in the embodiment of the PM sensor assembly 200 shown in FIGS. 8A and 8B. Specifically the intake apertures 244 may draw in a portion of exhaust gas at an upstream surface of the PM sensor assembly 200, and allow water droplets and larger particulates to exit the PM sensor assembly 200 at a downstream surface of the first outer tube 210.

Thus, the embodiment of PM sensor assembly 200 shown in FIGS. 8A and 8B may be the same as shown in FIGS. 7A and 7B in that it may be positioned within exhaust passage 48 and configured to sample exhaust gases flowing within. A portion of exhaust gases may flow into PM sensor assembly 200 and first outer tube 210 via apertures 244 proximate the base of the first outer tube 210. Water droplets and larger particulates may impinge on an exterior of the upstream surface 260 of the second inner tube 220 before circulating through an annular space formed between first outer tube 210 and second inner tube 220 and exiting out the apertures 244 positioned on the downstream surface of the first outer tube 210. The portion of exhaust gases may then enter the second inner tube 220 via apertures 246 on the second inner tube 220 and may impinge on the first surface 236 of PM sensor 232. The portion of exhaust gases may then exit the second inner tube 220 (and PM sensor assembly) via channels 242 on the bottom of the PM sensor assembly 200.

Turning now to FIG. 9A, it schematically shows a longitudinal sectional view 900 of the embodiments of PM sensor assembly 200 shown in FIGS. 7A and 7B, in a longitudinal plane along line D-D' of FIGS. 2, 7A and 7B. Thus, longitudinal sectional view 900 may be the same as longitudinal sectional view 300, except that it may show the embodiments of PM sensor assembly 200 shown in FIGS. 7A and 7B, instead of the embodiments shown in FIGS. 2A and 2B. As such, the only difference between longitudinal sectional view 900 and longitudinal sectional view 300 may be the positioning of the exit channels 242 on the PM sensor assembly 200. In the depicted example, PM sensor assembly 200 is coupled within exhaust pipe 310 (or conduit 310) and exhaust gases flow within area 320. Exhaust pipe 310 may be a portion of exhaust passage 48 in FIG. 1. Further, in the portrayed example of FIG. 3, exhaust gases are flowing towards the viewer within area 320. As such, the viewer is positioned downstream from PM sensor assembly 200 and is looking towards an upstream direction. Components previously introduced in FIGS. 1, 2A, 2B, 3, 7A and 7B, are numbered similarly in FIG. 9 and may not be reintroduced.

As described earlier in reference to FIGS. 7A, and 7B, second inner tube 220 may be fully enclosed within first outer tube 210. Annular space 364 may be formed between the first outer tube and the second inner tube. PM sensor 232 may be located within second inner tube 220 such that the first surface 236 with electrical circuit 234 faces the downstream direction (and the viewer). Second inner tube 220 may not be sealed across its bottom surface 264 (with respect to vertical) such that there may be one or more openings on bottom surface 264. Specifically, the openings on bottom surface 264 may be exit channels 242. Exit channels 242 may fluidically couple interior space 348 of second inner tube 220 with area 320 within exhaust pipe 310. Channels 242 may originate from bottom surface 264 of the second inner tube 220 and allow exhaust gases within interior space 348 to exit PM sensor assembly 200. Further, channels 242 may end on bottom surface 262 of first outer tube 210 of PM sensor assembly 200. Bottom surface 264 of the first outer tube, is substantially parallel to a direction of exhaust flow in the exhaust pipe 310. Further, bottom surface 262 of first outer tube 210 may be in direct contact with exhaust gases flowing in exhaust pipe 310.

Exhaust gasses within interior space 348 may exit second inner tube 220 via channels 242 and merge with rest of exhaust flow surrounding PM sensor assembly 200. Channels 242 are shown fluidically connecting interior space 348 of second inner tube 220 with the exhaust passage. Further, channels 242 do not fluidically connect annular space 364 with the exhaust passage and may be separated from annular space 364 by channel walls 328. Therefore, exhaust gases within annular space 364 may be blocked from channels 242 and may not exit annular space 364 via channels 242.

As shown in the example of FIG. 9A, the exit channels 242 may comprise one channel. However, in alternate embodiments, exit channels 242 may include a larger number of channels. The number of channels may also be based on the dimensions of the first outer tube 210 and the second inner tube 220.

Turning now to FIG. 9B, it schematically shows a longitudinal sectional view 950 of the embodiments of PM sensor assembly 200 shown in FIGS. 8A and 8B, in a longitudinal plane along line D-D' of FIGS. 2, 7A, 7B, 8A, and 8B. Thus, longitudinal sectional view 950 may be the same as longitudinal sectional view 900, except that it may show the embodiments of PM sensor assembly 200 shown in FIGS. 8A and 8B, instead of the embodiments shown in FIGS. 7A, and 7B. As such, the embodiments of the PM sensor assembly 200 shown in FIG. 9B may be different from that shown in FIG. 9A, in that the PM sensor assembly 200 in FIG. 9B may not include drainage holes 248 at the bottom surface 262 of the outer tube 210. Instead, intake apertures 244 which may be positioned around the circumference of the outer tube 210 as discussed above with reference to FIGS. 8A and 8B. However, the positioning of the one or more exit channels 242 may be the same as in FIG. 9A. In the depicted example, PM sensor assembly 200 is coupled within exhaust pipe 310 (or conduit 310) and exhaust gases flow within area 320. Exhaust pipe 310 may be a portion of exhaust passage 48 in FIG. 1. Further, in the portrayed example of FIG. 3, exhaust gases are flowing towards the viewer within area 320. As such, the viewer is positioned downstream from PM sensor assembly 200 and is looking towards an upstream direction. Components previously introduced in FIGS. 1, 2A, 2B, 3, 7A, 7B, 8A, 8B, and 9A are numbered similarly in FIG. 9 and may not be reintroduced.

Because the intake apertures 244 may extend around a circumference of the outer tube 210 in the embodiment of the PM sensor assembly 200 shown in FIGS. 8A, 8B, and 9B, the longitudinal sectional view 950 may include the intake apertures 244 on the outer tube 210. Specifically, as discussed above with reference to FIGS. 8A and 8B, the intake apertures 244, may be positioned more proximate the bottom surface 262 of the outer tube 210, than the top surface 250. A portion of exhaust gas flowing in exhaust pipe 310 may enter outer tube 210 into annular space 364 through the intake apertures 244. Additionally, water droplets and larger particulates may also exit the PM sensor assembly 200 through the intake apertures 244 on the outer tube 210. Therefore, the intake apertures 244 may also serve the function of the drainage holes 248 discussed above with reference to FIGS. 2A, 2B, 7A, 7B, and 9A. Thus, in the embodiment of PM sensor assembly 200 presented in FIGS. 8A, 8B, and 9B, the PM sensor assembly 200 may not include drainage holes 248.

All other aspects of the embodiment of PM sensor assembly 200 presented in FIG. 9B may be similar or the same as the embodiments of PM sensor assembly 200 shown previously in FIG. 9A.

For example, as described earlier in reference to FIGS. 8A, and 8B, second inner tube 220 may be fully enclosed within first outer tube 210. Annular space 364 may be formed between the first outer tube and the second inner tube. PM sensor 232 may be located within second inner tube 220 such that the first surface 236 with electrical circuit 234 faces the downstream direction (and the viewer). Second inner tube 220 may not be sealed across its bottom surface 264 (with respect to vertical) such that there may be one or more openings on bottom surface 264. Specifically, the openings on bottom surface 264 may be exit channels 242. Exit channels 242 may fluidically couple interior space 348 of second inner tube 220 with area 320 within exhaust pipe 310. Channels 242 may originate from bottom surface 264 of the second inner tube 220 and allow exhaust gases within interior space 348 to exit PM sensor assembly 200. Further, channels 242 may end on bottom surface 262 of first outer tube 210 of PM sensor assembly 200. Bottom surface 264 of the first outer tube, is substantially parallel to a direction of exhaust flow in the exhaust pipe 310. Further, bottom surface 262 of first outer tube 210 may be in direct contact with exhaust gases flowing in exhaust pipe 310.

Exhaust gasses within interior space 348 may exit second inner tube 220 via channels 242 and merge with rest of exhaust flow surrounding PM sensor assembly 200. Channels 242 are shown fluidically connecting interior space 348 of second inner tube 220 with the exhaust passage. Further, channels 242 do not fluidically connect annular space 364 with the exhaust passage and may be separated from annular space 364 by channel walls 328. Therefore, exhaust gases within annular space 364 may be blocked from channels 242 and may not exit annular space 364 via channels 242.

Figure 10:
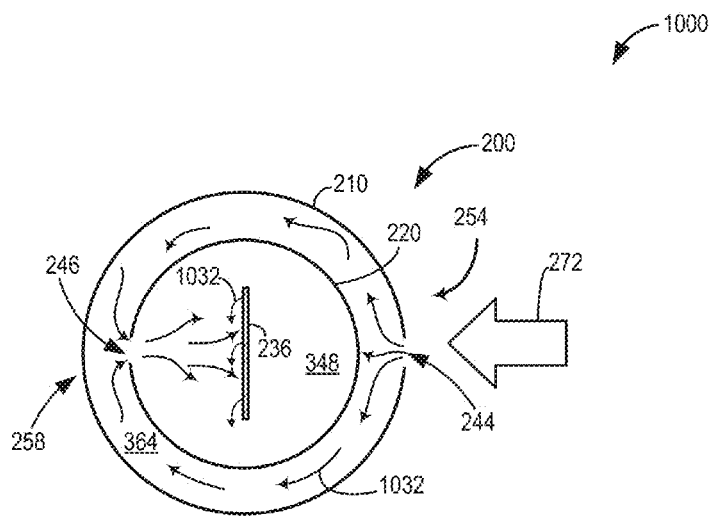
FIG. 10 shows a sectional view of the embodiments of the PM sensor assembly shown in FIGS. 7A-7B as placed in an exhaust passage of the engine of FIG. 1.

As shown in the example of FIG. 9B, the exit channels 242 may comprise one channel. However, in alternate embodiments, exit channels 242 may include a larger number of channels. The number of channels may also be based on the dimensions of the first outer tube 210 and the second inner tube 220. FIG. 10. schematically shows a cross sectional view of the embodiment of PM sensor assembly 200 shown in FIGS. 7A and 7B along plane, A-A.' As such, components previously introduced in FIGS. 2-7 are similarly numbered and not reintroduced.

Referring to FIG. 10, it shows a cross sectional view 1000 along plane A-A' of FIGS. 7A and 7B wherein the view (1000) includes a section across PM sensor assembly with one or more upstream intake apertures 244 facing oncoming exhaust flow, and one or more downstream intake apertures 246 on second inner tube. An example sampling method via PM sensor assembly 200 will be elaborated in detail below in reference to FIGS. 2-8.

As exhaust gases flow from right hand side to left hand side of FIG. 4A, a portion of exhaust gases 432 may enter PM sensor assembly 200 via the one or more intake apertures 244 at upstream surface 254 of first outer tube 210. The portion of exhaust gases 1032 may strike the exterior of the upstream surface 260 of second inner tube 220 before being transported through annular space 364, formed between an interior surface of first outer tube 210 and an exterior surface of second inner tube 220. Thus, second inner tube 220 may act as an insulation shield for PM sensor 232 reducing heat loss from PM sensor 232 during regeneration. The portion of exhaust gases 1032 may be streamed towards the downstream end of annular space 364.

The portion of exhaust gases 1032 may comprise water droplets, e.g. from the DPF, and larger particulates along with other dispersed constituents. In one example, these water droplets and larger particulates may be deposited on upstream surface 260 of second inner tube 220 upon impingement of the portion of exhaust gases 1032. Herein, the deposited water droplets and larger particulates may sink to the bottom surface of first outer tube 210 and drain out through drainage holes 248 (not shown in FIG. 10). In another example, the water droplets and larger particulates may be transported through annular space 364.

The portion of exhaust gases 1032 may then enter interior space 348 within second inner tube 220 via the one or more intake apertures 246 on downstream surface of second inner tube 220. Herein, the portion of exhaust gases 1032 changes direction of flow by 180 degrees to enter second inner tube 220 from annular space 364. In this example, water droplets and larger particulates may not be able to change their flow direction due to their higher momentum and may be deposited on an interior downstream surface of first outer tube 210. These particulates and droplets may eventually gravitate towards bottom surface 262 of first outer tube 210 and may drain out of drainage holes 248.

As the portion of exhaust gases 1032 enters second inner tube 220 via intake apertures 246, the exhaust gases may impinge on first surface 236 of PM sensor 232. By impinging the exhaust gases onto the surface of the PM sensor, instead of flowing exhaust gas samples across the surface of the PM sensor, uniformity of PM deposition may be enhanced. As described earlier in reference to FIG. 2, first surface 236 may feature electrical circuit 234 so that particulates, such as soot, may be deposited on first surface 236 and may be detected via electrical circuit 234. The portion of exhaust gases 1032 may then exit interior space 348 of second inner tube 220, and therefore, the PM sensor assembly 200 via channels 242 (not shown) at the bottom of the PM sensor assembly. After impinging on the PM sensor 232, the portion of exhaust gasses 1032 may turn 90 degrees downward and flow toward the bottom of the PM sensor assembly 200 and exit at the bottom surfaces 264 and 262 of the PM sensor assembly 200.

Thus, the flow of the exhaust gasses 1032 in FIG. 10 may be different than the flow of exhaust gasses 432 in FIG. 4, in that after impinging on the PM sensor 232, instead of flowing out through the side surfaces 256 of the PM sensor assembly as in FIG. 4, the exhaust gas may exit at the bottom surfaces 264 and 262 of the PM sensor assembly 200. Said another way the only difference in the flow of exhaust gas between FIG. 4 and FIG. 10, is that in FIG. 10 exhaust gas may exit the PM sensor assembly 200 through the bottom and not the sides.

Thus, when the portion of exhaust gases 1032 enters PM sensor assembly 200, it may flow first into the first outer tube 210, next into second inner tube 220, and subsequently exit the PM sensor assembly via channels 242 which may be positioned at the bottom of the PM sensor assembly. The portion of exhaust gases 1032 may, therefore, not enter the second inner tube 220 directly. Further, the portion of exhaust gases 1032 may not exit from the first outer tube 210 other than by flowing through second inner tube 220. Intake apertures 244 fluidically couple the exhaust passage to the annular space 364 within first outer tube 210, and intake apertures 246 fluidically couple annular space 364 to interior space 348 within second inner tube 220. Further, channels 242 fluidically couple interior space 348 within second inner tube 220 to the exhaust passage.

Even though first outer tube 210 includes drainage holes 248, the bulk portion of exhaust gases 1032 may flow from annular space 364 within first outer tube 210 into interior space 348 of second inner tube 220 because of momentum and static pressure.

It will be appreciated that the portion of exhaust gases 1032 may undergo three changes in flow direction: a first change in direction as the portion of exhaust gases enter the first outer tube 210 and turn to flow around annular space 364, a second change in direction as the portion of exhaust gases 1032 enters second inner tube 220 from apertures 246, and a third change in direction as the portion of exhaust gases 1032 impinges upon PM sensor and turns downward to exit the PM sensor assembly. These changes in flow direction may improve evenness of flow and also reduce flow rate within the PM sensor assembly.

Figure 11:
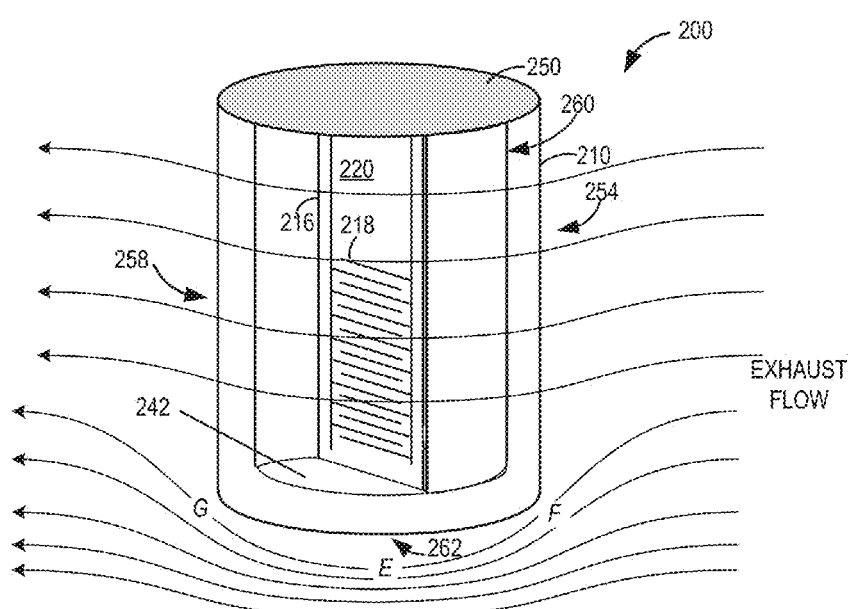
FIG. 11 is an example fluid flow around the PM sensor assembly.

Turning now to FIG. 11, fluid (e.g., exhaust gas) flow around PM sensor assembly 200 in exhaust passage (e.g., exhaust passage 48) is shown. In the example shown in FIG. 11, exhaust gas in the exhaust passage flows from right to left. The location marked "F" corresponds to upstream surface 254 of first outer tube 210, the location marked "G" corresponds to downstream surface 258 of first outer tube 210, and location marked "E" corresponds to bottom surface 262 of first outer tube 210 of PM sensor assembly 200. Gas flow around PM sensor assembly 200 and specifically, first outer tube 210, causes a static pressure variation along the exterior of the sensor assembly. A higher static pressure may exist at upstream location F while a lower static pressure may exist at bottom surface E. Further, static pressure at location G may be higher than that at bottom location E but lower than static pressure at location F. In other words, positioning intake apertures at location F (and to a smaller extent, location G) and exit channels at bottom location E may be more advantageous for sampling exhaust gases. The low static pressure at bottom location E naturally draws out exhaust gases from within PM sensor assembly while the higher static pressure at location F (and to a smaller extent, location G) may enable an easier drawing in of exhaust gases into PM sensor assembly. In the embodiments described herein, intake apertures and exit channels may be positioned to take advantage of this effect.

Figure 12:
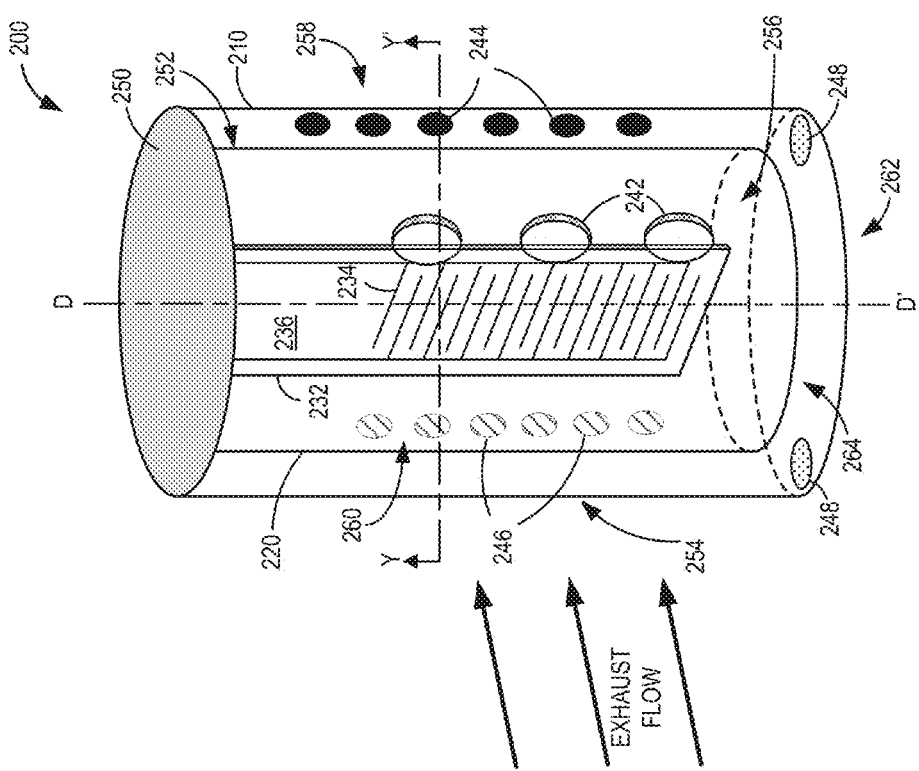
FIG. 12 is a schematic illustration of an alternative embodiment of the PM sensor assembly of FIG. 2.

Turning now to FIG. 12, it portrays an alternative embodiment of the PM sensor assembly 200 of FIGS. 2-10. The embodiment of PM sensor assembly 200 presented in FIG. 12 may be the same is in the embodiment of PM sensor assembly 200 presented in FIG. 2A, but is arranged in an exhaust passage (e.g., exhaust passage 48) in an opposite orientation. Specifically, PM sensor assembly 200 is arranged such that the intake apertures on the first outer tube are on the downstream surface 254 of the first outer tube 210. Additionally, intake apertures on the second inner tube are positioned on the upstream surface 260 of the second inner tube 220. In other words, PM sensor assembly 200 may be the same as the embodiment of PM sensor assembly 200 shown in FIG. 2A, except that it may be positioned in reverse orientation with respect to a direction of exhaust flow from the DPF. Said another way, the positions of the intake apertures 244 and 246 may be positioned at different locations on the first outer tube 210 and second inner tube 220, respectively, in the embodiment of the PM sensor assembly 200 presented in FIGS. 12-13, than in the embodiments of the PM sensor assembly previously shown in FIGS. 2-8.

In the embodiment shown in FIG. 12, exhaust gases flow from the left hand side to the right hand side of FIG. 12. Thus, PM sensor assembly 200 is portrayed from an upstream perspective. An arrangement such as the one in FIG. 12 may be used in engines with larger displacements wherein an exhaust mass flow rate may be higher whereas the embodiment of FIGS. 2-10, may be used in engines with smaller displacements.

Figure 13:
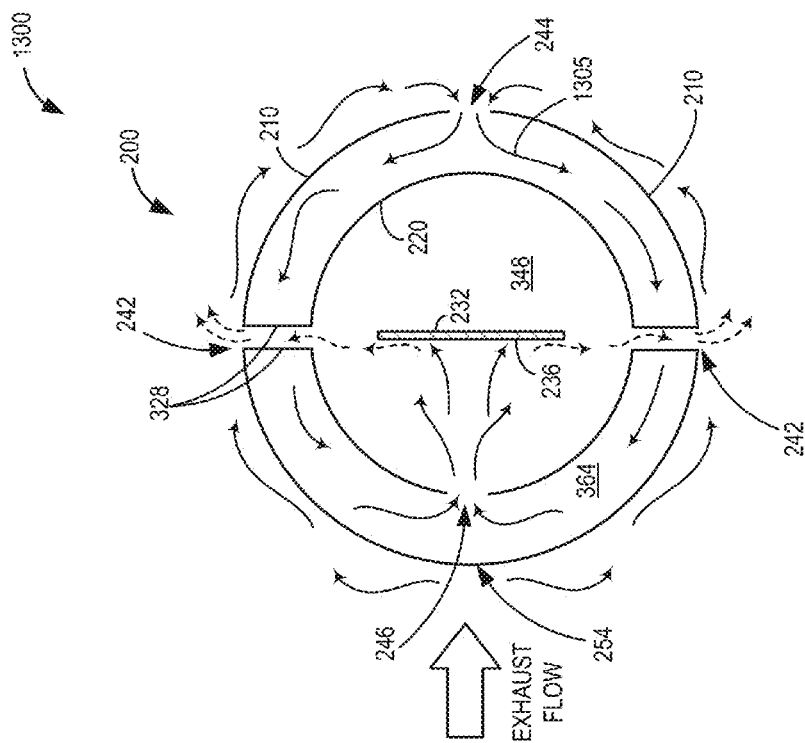
FIG. 13 depicts a cross sectional view of the embodiment of the PM sensor assembly shown in FIG. 12.

The operation of the embodiment of PM sensor assembly 200 shown in FIG. 12 will be described herein in reference to FIGS. 12 and 13. FIG. 13 is a cross sectional view 1300 in a cross sectional plane along line D-D' of FIG. 12. Further, cross sectional view 1300 includes one or more intake apertures 244 on first outer tube, the one or more intake apertures 246 on second inner tube, and exit channels 242.

A portion of exhaust gases 1305 may enter PM sensor assembly 200 from intake apertures 244 which in the example of PM sensor assembly 200 shown in FIGS. 12-13 may be located on the downstream surface 258 of first outer tube 210 facing away from the flow of exhaust in the exhaust passage, and not on the upstream surface 254 as shown in the examples in FIGS. 2-7. Downstream surface 258 is substantially normal to and facing away from exhaust flow. In the example of PM sensor assembly 200 shown in FIGS. 12-13, the PM sensor assembly 200 may not include intake apertures on an upstream surface 254 of first outer tube 210 which may be facing oncoming exhaust flow. Further, the portion of exhaust gases 1305 may enter PM sensor assembly 200 in an un-impeded manner.

The portion of exhaust gases 1305 may then be guided through annular space 364 to apertures 246 which in the example of PM sensor assembly 200 shown in FIGS. 12-13 may be located on an upstream surface 260 of second inner tube 220. The exhaust gasses 1305 may then be admitted into interior space 348 within second inner tube 220. Upstream surface 260 of second inner tube 220 may be substantially normal to and facing the direction of exhaust flow. However, upstream surface 260 of second inner tube 220 may not be in direct contact with the exhaust flow in the exhaust passage since second inner tube is enclosed within first outer tube 210. On the other hand, second inner tube 220 may be in direct contact with the portion of exhaust gases 1305 within PM sensor assembly 200.

Upon entering interior space 348, the portion of exhaust gases 1305 may impinge onto PM sensor 232. An electrical circuit 234 may be located on a first surface 236 of PM sensor 232. Further, PM sensor 232 may be positioned within second inner tube 220 such that first surface 236 and electrical circuit 234 are facing the apertures 246 on second inner tube 220. Specifically, first surface 236 of PM sensor 232 may face an incoming flow of the portion of exhaust gases 1305 allowing for a more uniform deposition of PM.

After impinging upon PM sensor 232, the portion of exhaust gases 1305 may exit the PM sensor assembly 200 via channels 242 on side surfaces 256. The portion of exhaust gases 1305 exiting the PM sensor assembly 200 is represented by dotted lines to differentiate it from the exhaust gas flow existing outside of PM sensor assembly 200. Channels 242 fluidically couple second inner tube 220 with the exhaust passage. Specifically, interior space 348 within second inner tube 220 may be fluidically connected, without blockages, to the exhaust passage. Accordingly, clear passage for the portion of exhaust gases within interior space 348 may be enabled allowing a flow of the portion of exhaust gases from within the second inner tube 220 into the exhaust passage. It will be appreciated that channels 242, may not fluidically couple first outer tube 210 to the exhaust passage. Specifically, channels 242 do not fluidically communicate with annular space 364. Channels 242 may include walls 328 that block fluidic communication between first outer tube 210 (and annular space 364), and exhaust passage.

Further, first outer tube 210 may include drainage holes 248 to allow the removal of water droplets and/or larger particulates that may be accumulated on either the interior upstream surface of first outer tube 810 or on the exterior downstream surface of second inner tube 220. Larger particulates and/or water droplets entering first outer tube 210 may have higher momentum that reduces their transport into second inner tube 220 via the change in flow direction at apertures 246. Further, water droplets and larger particulates may also impinge upon exterior downstream surface of second inner tube 220 as the portion of exhaust gases 1305 enters the first outer tube 210. Consequently, these particulates and droplets may accumulate and settle downwards near the bottom surface 262 (with respect to vertical) of first outer tube 210, and drain out through drainage holes 248.

All other aspects of the embodiment of PM sensor assembly 200 presented in FIGS. 12-13 may be similar or the same as the embodiments of PM sensor assembly 200 shown previously in FIGS. 2-10.

For example, second inner tube 220 may be positioned concentrically within first outer tube 210. Thus, a central axis of second inner tube 220 may be parallel to, or coincide with, a central axis of first outer tube 210. In the example of FIG. 12, the central axis of second inner tube 220 may coincide with and be the same as central axis X-X' of first outer tube 210. In alternate embodiments, the central axis may not coincide but may be parallel.

Thus, the embodiment of PM sensor assembly 200 depicted in FIGS. 12 and 13 may be a system comprising a first outer tube with a plurality of intake apertures on a downstream surface, a second inner tube with a plurality of intake apertures on an upstream surface, and a particulate matter sensor placed within the second inner tube. Further, the second inner tube is positioned within the first outer tube such that a central axis of the second inner tube is parallel with a central axis of the first outer tube and an annular space exists between the second inner tube and the first outer tube. Additionally, the particulate matter sensor is positioned within the second inner tube such that a first surface of the particulate matter sensor with an electrical circuit faces the plurality of gas intake apertures on the upstream surface of the second inner tube. The first outer tube has a plurality of drainage holes at a bottom surface with respect to vertical while a bottom surface of the second inner tube is sealed. Furthermore, one or more channels fluidically connect the second inner tube to the exhaust passage of the engine and do not connect the first outer tube to the exhaust passage.

Figure 14:
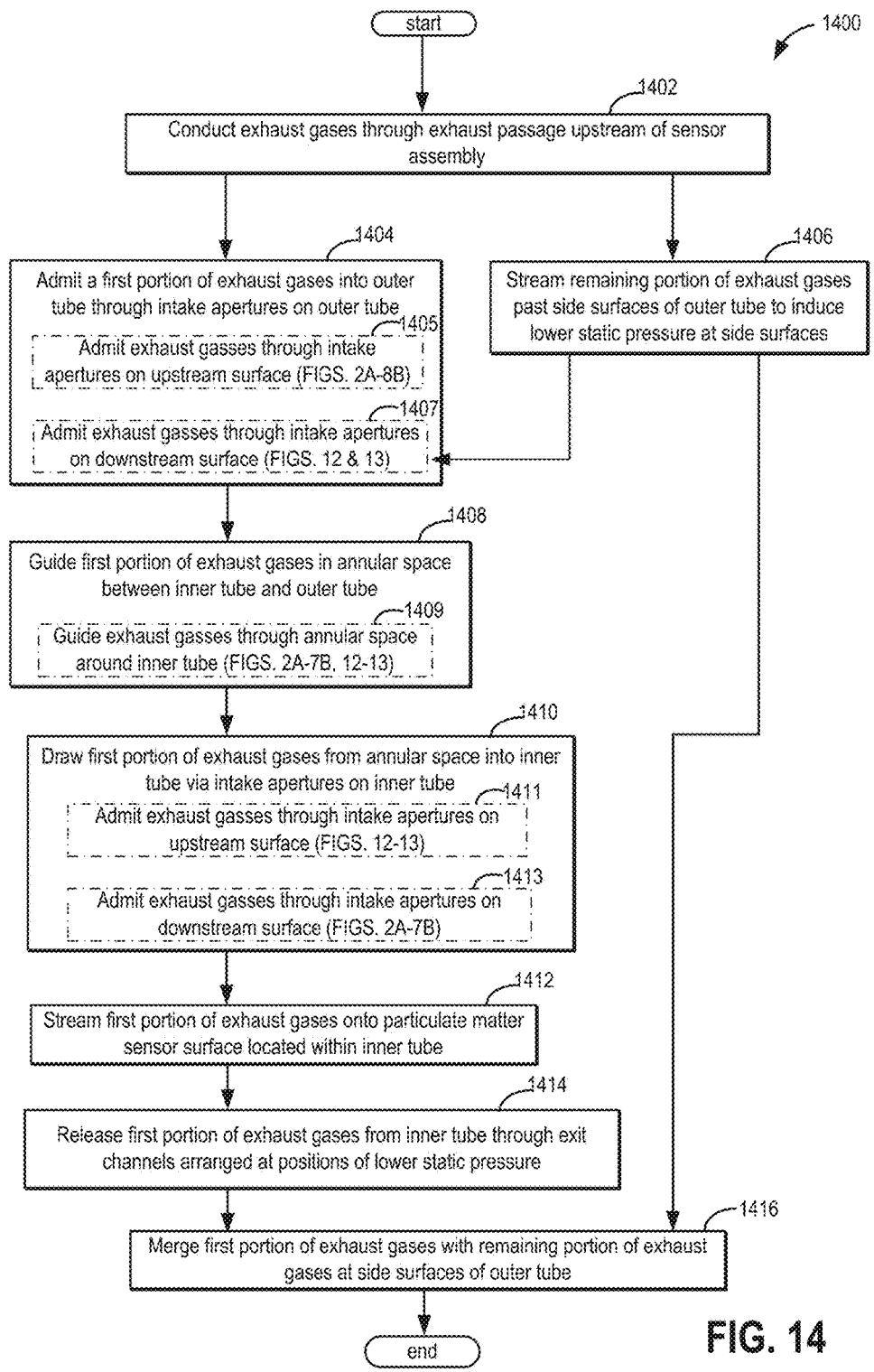
FIG. 14 is an example flowchart of a method for sensing PM using the PM sensor assembly of FIGS. 1-2, 7A-7B, 8A-8B, and 12.

Turning now to FIG. 14, an example routine 1400 for sensing particulate matter is shown. The PM sensor assembly described in reference to FIGS. 2-13 may be used to detect particulate matter within exhaust gases exiting a DPF. For example, DPF leakage may be detected by the PM sensor assembly based on a sensed concentration of particulate matter within exhaust gases.

At 1402, exhaust flow may be conducted through an exhaust passage upstream of PM sensor assembly (e.g., PM sensor assembly 200). At 1404, a first portion of exhaust gases may be admitted into the first outer tube (e.g., first outer tube 210) via intake apertures (e.g. intake apertures 244) located on the first outer tube. In one example, 1404 may include, as exhaust gases flow through an exhaust passage of an engine and past the PM sensor assembly, admitting a portion of exhaust gasses in the first outer tube via a set of intake apertures on an upstream surface of first outer tube at 1405. Thus, routine 1400 may proceed to 1405 if the PM sensor assembly is similar to the PM sensor assembly 200 shown in FIGS. 2-8, and comprises intake apertures on an upstream surface of the PM sensor assembly. In another example, 1404 may include, flowing exhaust around the PM sensor assembly and admitting a portion of exhaust gasses in the first outer tube via a set of intake apertures on a downstream surface of first outer tube at 1407. Thus, routine 1400 may proceed to 1407 after 1406 as described in greater detail below if the PM sensor assembly is similar to the PM sensor assembly 200 shown in FIGS. 12-13, and comprises intake apertures on a downstream surface of the PM sensor assembly. Simultaneously, at 1406, the remaining portion of exhaust gases (e.g., exhaust gases other than the first portion entering the PM sensor assembly) may stream past the side surfaces of the PM sensor assembly. As such, the exhaust gases may flow past the first outer tube of the PM sensor assembly and induce a lower static pressure at the side surfaces (e.g., side surfaces 256) and bottom surface (e.g., bottom surface 262) of the PM sensor assembly as described in reference to FIGS. 6 and 11. As described above, if the PM sensor assembly contains downstream intake apertures, routine 1400 may proceed from 1406 to 1407, and admit a portion of the exhaust gas that has flowed past the sensor assembly through intake apertures on a downstream surface. As explained above in reference to FIG. 6, a higher static pressure may exist at the downstream surface of the PM sensor assembly than at its side surfaces. Thus, exhaust gases flowing past the PM sensor assembly may get drawn into the first outer tube at its downstream surface.

At 1408, the first portion of exhaust gases admitted into the first outer tube may be guided through the annular space formed between an interior surface of first outer tube and an exterior surface of second inner tube (e.g., second inner tube 220). In one example, the first portion of exhaust gases may be led to the downstream end of PM sensor assembly at 1409. Herein, heavier, larger particulates and/or water droplets that may be included in the first portion of exhaust gases may be deposited on either the interior surface of first outer tube or on the exterior surface of second inner tube. Next, at 1410, the first portion of exhaust gases may be admitted into the second inner tube via apertures (e.g., apertures 246) located on the second inner tube. In one example, 1410 may include, admitting a portion of exhaust gasses in the second inner tube via a set of intake apertures on an upstream surface of second inner tube at 1411. Thus, routine 1400 may proceed to 1411 if the PM sensor assembly is similar to the PM sensor assembly 200 shown in FIGS. 12-13, and comprises intake apertures on an upstream surface of the first inner tube of the PM sensor assembly. In another example, 1410 may include, admitting a portion of exhaust gasses in the second inner tube via a set of intake apertures on a downstream surface of second inner tube at 1413. Thus, routine 1400 may proceed to 1413 if the PM sensor assembly is similar to the PM sensor assembly 200 shown in FIGS. 2-8, and comprises intake apertures on a downstream surface of the inner first tube of the PM sensor assembly.

At 1412, the first portion of exhaust gases may impinge on a surface of the PM sensor comprising an electrical circuit.

Further, soot and other particulates within the first portion of exhaust gases may be deposited on the surface of the PM sensor. Further still, the controller may receive feedback from the PM sensor. Next, at 1414, the first portion of exhaust gases may be released from second inner tube through exit channels arranged at lower static pressures. As described earlier at 1406, a lower static pressure may be induced at side surfaces and bottom surface of the first outer tube by remaining exhaust gases flowing past the first outer tube of PM sensor assembly. The lower pressure may assist in drawing out the first portion of exhaust gases from the PM sensor assembly. Thus, in one example, the exit channels may positioned at the bottom of the PM sensor assembly as in FIGS. 7-8, and as such the exhaust gas may exit the PM sensor assembly through the bottom of the sensor assembly. In another example, the exhaust gas at 1414 may exit through channels positioned on the side surfaces of the PM sensor assembly. Thus, for PM sensor assemblies as shown in FIGS. 2A and 2B with exit channels positioned at side surfaces, exhaust gas at 1414 may exit through the sides of the PM sensor assembly. At 1416, the first portion of exhaust gases exiting the PM sensor assembly may merge with remaining exhaust gases flowing past the PM sensor assembly.

In this way, a method for sensing particulate matter in an exhaust passage comprises directing a portion of exhaust gas into a first outer tube through a first plurality of perforations on a first outer tube, guiding the portion of exhaust gas into a second inner tube through a second plurality of perforations on a second inner tube, and flowing the portion of exhaust gas onto a particulate matter sensor located within the second inner tube. The method further comprises guiding the portion of exhaust gas out of the second inner tube via exit channels into the exhaust passage.

In this way, a system for sensing particulate matter in an exhaust passage of an engine may comprise a first outer tube with one or more gas intake apertures, a second inner tube including one or more intake apertures and arranged within the first outer tube, a central axis of the second inner tube parallel to a central axis of the first outer tube, a particulate matter sensor positioned within the second inner tube and having an electrical circuit on a first surface, and one or more exit channels fluidically connecting only the second inner tube and not the first outer tube to the exhaust passage. The one or more intake apertures of the first outer tube may further comprise a single rectangular aperture positioned on an upstream surface of the first outer tube, the upstream surface including a surface normal to and facing a flow of exhaust gases in the exhaust passage. Alternatively, the one or more intake apertures of the first outer tube may further comprise a plurality of circular apertures positioned around a circumference of the first outer tube. In another example, the one of more intake apertures of the first outer tube may further comprise a plurality of circular apertures positioned along an axis parallel to the central axis of the first outer tube. The one or more intake apertures of the second inner tube may further comprise a single rectangular aperture with a first pair of parallel sides longer than a second pair of parallel sides, the first pair of parallel sides parallel to the central axis of the second inner tube. In another example, the one or more intake apertures of the second inner tube may further comprise a plurality of circular apertures aligned along an axis parallel to the central axis of the second inner tube. The particulate matter sensor may be placed within the second inner tube such that the first surface with the electrical circuit faces the one or more intake apertures of the second inner tube. The exit channels may originate from side surfaces of the second inner tube, each side surface being tangential to a direction of exhaust flow in the exhaust passage. The exit channels may alternatively originate from a bottom surface of the second inner tube, the bottom surface being parallel to a direction of exhaust flow in the exhaust passage.

Turning now to FIGS. 15A and 15B, they portray a PM sensor assembly 1500. Specifically, PM sensor assembly 1500 features a single protective tube surrounding a PM sensor 1532 unlike PM sensor assembly 200 which features two protective tubes around their respective PM sensors.

In the embodiment shown in FIGS. 15A and 15B, exhaust gases flow from the right hand side to the left hand side of FIGS. 15A and 15B. Thus, PM sensor assembly 1500 is viewed from a downstream perspective. The PM sensor assembly 1500 may be positioned in an exhaust passage such that a central axis M-M' of the PM sensor assembly 1500 may be perpendicular to the flow of exhaust gas in the exhaust passage.

PM sensor assembly 1500 includes a protective tube 1520 with a plurality of intake apertures 1546 on a downstream surface 1552 of protective tube 1520. Specifically, the downstream surface 1552 of the protective tube 1520, may be normal to and facing away from the flow of exhaust gas in the exhaust passage. Thus, in the example shown in FIGS. 15A and 15B, with the exhaust gas flowing from right to left, the intake apertures 1546, may be positioned on the left side of protective tube 1520, such that exhaust gasses must flow around the protective tube 1520 before entering the intake apertures 1546. Intake apertures 1546 may serve as intake apertures for sampling exhaust gases for particulate matter. As shown in the example of FIGS. 15A and 15B, intake apertures 1546 may comprise a plurality of circular apertures aligned with one another along a vertical axis of the first outer tube 210 parallel to a central axis M-M' of the first outer tube 210. In one example, the intake apertures may be aligned in a single column along the downstream surface 1552 of the protective tube 1520. In other examples, the intake apertures may be aligned in more than one column along the downstream surface 1552 of the protective tube 1520. In further examples, the apertures 1546 may extend from a bottom surface 1562 to a top surface 1550 of the protective tube 1520. In other examples, the apertures 1546 may not extend from the bottom surface 1562 to the top surface 1550 and may be fully contained within the downstream surface 1552. An upstream surface 1554 of protective tube 1520 is substantially normal to and faces oncoming exhaust gas flow. Protective tube 1520 also includes multiple exit apertures 1548 on its side surfaces 1556. As shown in the example of FIG. 15A, exit apertures 1548 may comprise a plurality of circular apertures aligned with one another along a vertical axis of the protective tube 1520 parallel to a central axis M-M' of the first outer tube 210. However in another embodiment, as shown in FIG. 15B, the exit apertures 1548 may be rectangular. Specifically, the one or more exit apertures 1548 may be rectangles with a first pair of parallel sides longer than a second pair of parallel sides. Further the exit apertures 1548 as shown in FIG. 15B, may be positioned on the protective tube 1520, such that the first pair of parallel sides are parallel to the central axis M-M' of the protective tube 1520. In one example, the exit apertures 1546 may comprise only one rectangular aperture as shown in FIG. 15B. However, in other examples, the exit apertures 1548 may comprise more than one rectangular aperture. Specifically, one rectangular aperture may be positioned proximate the top surface 1550 while another rectangular aperture may be positioned proximate the bottom surface

1562. However, other positions of the rectangular apertures are possible. As an example, the exit apertures 1548 may be evenly spaced from one another. Further, a PM sensor 1532 may be positioned within protective tube 1520. A first surface 1536 of PM sensor 1532 may feature an electrical circuit 1534, and PM sensor 1532 may be arranged within protective tube 1520 such that the first surface 1536 faces downstream intake apertures 1546. Thus, the electrical circuit 1534 may be exposed to an incoming flow of exhaust gases from downstream intake apertures 1546. PM sensor 1532 may be positioned within protective tube 1520 such that a central, longitudinal axis of PM sensor 1532 is parallel to a central axis of protective tube 1520. In the example shown in FIG. 11, the central axis of PM sensor 1532 and protective tube 1520 may coincide at axis M-M'. Thus, the PM sensor 1532 may be positioned centrally within the protective tube 1520. Alternate arrangements of PM sensor 1532 within protective tube 1520 may be used in other embodiments.

PM sensor assembly 1500 may be sealed at its top surface 1550 (with respect to vertical) by the wall of the exhaust passage, similar to PM sensor assembly 200. As such, a sealed joint between a wall of exhaust passage and PM sensor assembly 1500 may be achieved to reduce leakage of exhaust gases from exhaust passage into the atmosphere. Further, bottom surface 1562 of protective tube 1520 may be closed and sealed. Specifically, the PM sensor assembly may be formed in a manner such that the sole openings on protective tube 1520 are intake apertures 1546 and exit apertures 1548. In other examples, the bottom surface 1562 may include one or more drainage holes 1548 similar to drainage holes 248 of PM sensor assembly 200 to allow water droplets and larger particulates to exit the PM sensor assembly 1500.

Thus, the PM sensor of FIGS. 15A and 15B includes a system comprising a PM sensor enclosed within a protective tube, the protective tube having a plurality of exhaust gas intake apertures on a downstream surface of the protective tube and a plurality of exit apertures on side surfaces of said protective tube. Further, the PM sensor may be arranged within the protective tube such that a central axis of PM sensor is parallel to a central axis of the protective tube. Additionally, the PM sensor may have an electrical circuit on a first surface and the PM sensor may be positioned within the protective tube such that the first surface faces the plurality of exhaust gas intake apertures on the downstream surface of the protective tube.

FIG. 16 shows a cross sectional view 1600 along plane Z-Z' of PM sensor assembly 1500 of FIG. 15. Cross sectional view 1600 along plane Z-Z' includes a downstream intake aperture 1546 and an exit aperture 1548 on protective tube 1520. Exhaust flows from right hand side of FIG. 16 to left hand side of FIG. 16.

As exhaust gases flow past PM sensor assembly 1500 in an exhaust passage, a portion of exhaust gases 1664 may enter PM sensor assembly 1500 through downstream intake apertures 1546 of protective tube 1520. Specifically, the portion of exhaust gases may enter into an interior space 1642 enclosed within protective tube 1520. As explained earlier in reference to FIGS. 5 and 6, a higher static pressure (with low velocity) may be induced at a downstream end of PM sensor assembly 1500 when exhaust gases flow past the PM sensor assembly 1500. This higher static pressure may assist in inducing the entry of the portion of exhaust gases 1664 into PM sensor assembly 1500.

The portion of exhaust gases 1664 that enter interior space 1642 may impinge onto first surface 1536 of PM sensor 1532. Further, the portion of exhaust gases may exit the PM sensor assembly 1500 via exit apertures 1548 on side surfaces 1556 and merge with exhaust gases as they flow past the sensor. The portion of exhaust gases 1664 exiting from the PM sensor assembly are shown as dotted lines to differentiate them from the remaining exhaust gases in the exhaust passage flowing past the PM sensor assembly 1500. As described earlier in reference to FIGS. 5 and 6, exhaust gases flowing past the protective tube 1520 may induce regions of lower static pressure at side surfaces 1556 of protective tube 1520. These regions of lower static pressure may draw out the portion of exhaust gases 1664 from within the interior space 1642 of protective tube 1520.

The sizes and location of exhaust gas intake apertures 1546 may be optimized by using a model, such as a computational fluid dynamics (CFD) tool, to enable a more uniform flow rate across first surface 1536 of PM sensor 1532. By enabling a more uniform flow rate of the portion of exhaust gases 1664 onto PM sensor 1532, a more uniform deposition of particulates may occur on first surface 1536. Further, by using a PM sensor assembly such as PM sensor assembly 1500, the portion of exhaust gases 1664 may be sampled from a location closer to a central axis of the exhaust passage instead of sampling exhaust gases closer to a periphery of the exhaust passage. Exhaust gases at the center of the exhaust passage may contain particulate matter concentration that is more representative of average particulate matter concentration. Therefore, the accuracy of output from PM sensor may be increased.

Turning now to FIG. 17, fluid (e.g., exhaust gas) flow around PM sensor assembly 1500 in a portion of an exhaust passage 1705 is shown. As shown in FIG. 17, exhaust gas may flow in the exhaust passage 1705 from right to left. The location marked "L" corresponds to upstream surface 1554 of protective tube 1520, the location marked "M" corresponds to downstream surface 1552 of protective tube 1520, and locations marked "N" and "O" correspond to side surfaces 1556 of protective tube 5120 of PM sensor assembly 1500. Gas flow around PM sensor assembly 1500 and specifically, protective tube 1500, causes a static pressure variation along the exterior of the sensor assembly. Further, a higher static pressure may exist at upstream location L, while a lower static pressure may exist at each of exterior side surfaces N and O. Further, static pressure at location M may be higher than that at side surfaces N and O but lower than static pressure at location L. In other words, positioning intake apertures at location M and exit channels at side surfaces N and O may be more advantageous for sampling exhaust gases. In the embodiments described herein, intake apertures and exit channels may be positioned to take advantage of this effect. The low static pressure at location N and O naturally draw out exhaust gases from within PM sensor assembly while the higher static pressure at location M may enable an easier drawing in of exhaust gases into PM sensor assembly. Thus, because a viable conduit is provided for exhaust gasses to travel from location M to locations O and N through intake apertures 1546 (shown in FIG. 16), and exit channels 1548 (shown in FIG. 16), a portion of exhaust gas as shown in FIG. 17, may be drawn back towards the PM sensor assembly after having flowed past it. Positioning intake apertures at location M may be more advantageous than at location L, because the flow of exhaust gasses into the protective tube 1520 and onto the PM sensor 1532 may be more evenly controlled. Specifically, the flow speed of the portion of the exhaust gas entering the protective tube 1520 may be reduced if entering at location M as opposed to location L. This may be due to the fact that exhaust gas entering at location M may reverse its flow direction as shown in FIG. 17. In other words, after flowing past the protective tube 1520, a portion of exhaust gas may reverse its flow, and turn back toward the downstream surface of the protective tube 1520, if a suitable conduit is provided for the exhaust gasses to travel from location M to N and O. Said another way, after traveling around the PM sensor assembly 1500 from right to left, a portion of exhaust gas may reverse direction by 180 degrees and be drawn back through the PM sensor assembly via intake apertures 1546 and exit channels 1548. In addition, to creating more controlled flow, and thus more even soot deposition on the PM sensor 1532 by positioning intake apertures at location M as opposed to location L, the amount of water droplet and larger particulate deposition on the PM sensor 1532 may also be reduced.

The amount of water droplets, and larger particulates entering the PM sensor assembly may be reduced as compared to having intake apertures on the upstream surface of the PM sensor assembly. Because of their larger momentum compared to the exhaust gas, it may be more difficult for water droplets, and larger particulates to reverse their flow direction and flow back towards the PM sensor assembly 1500 after having traveled past it.

In this way a system may comprise, an engine exhaust passage, and a particulate matter sensor positioned within a protective tube in the passage, the protective tube having intake apertures located on a downstream surface, and exit channels located on side surfaces, the particulate matter sensor having an electrical circuit on a first surface positioned within the protection tube such that the first surface faces the one more gas intake apertures. The downstream surface may include a surface normal to and facing away from the flow of exhaust gasses in the exhaust passage, side surfaces tangential to the flow of exhaust gasses in the exhaust passage. The intake apertures of the protection tube may comprise a plurality of circular apertures positioned along an axis parallel to a central axis of the protection tube. Alternatively, the exit channels may comprise rectangular apertures where each aperture comprises a first pair of parallel sides longer than and orthogonal to a second pair of parallel sides, and where the first pair of parallel sides are parallel to a central axis of the protection tube. The exit channels may comprise circular apertures positioned along an axis parallel to a central axis of the protection tube. The protection tube may be sealed at top with respect to vertical when coupled in an exhaust system of a vehicle traveling on a road. The system may further comprise drainage holes positioned on a bottom surface of the protection tube.

Turning now to FIG. 18, a method of sampling exhaust gases using PM sensor assembly 1500 is shown. Specifically, a sample of exhaust gases is drawn in from intake apertures on a downstream surface of the protective tube and allowed to impinge on a PM sensor surface.

At 1802, exhaust gases may be conducted through an exhaust passage past the PM sensor assembly. As such, exhaust gases may be flowing with the exhaust passage from upstream of PM sensor assembly to downstream of PM sensor assembly. Thus, the PM sensor assembly may be positioned in an exhaust passage where exhaust gas may be flowing in one direction. Thus at 1802, exhaust may flow in one direction from upstream of the PM sensor assembly to downstream of the sensor assembly. At 1804, a portion of exhaust gases may be drawn into the protective tube (e.g., protective tube 1520) of PM sensor assembly. Specifically, the portion of exhaust gases may enter the protective tube through a plurality of intake apertures (e.g., apertures 1546) on a downstream surface (e.g., surface 1552) of the protective tube. As explained above with reference to FIG. 17, a lower static pressure may exist at side surfaces (e.g., side surfaces 1556) of the protective tube relative to the downstream surface, and as such, exhaust gas may be drawn back toward the downstream surface of the protective tube and out the exit channels positioned on the side surfaces of the protective tube. Said another way, due to the lower pressure that exists directly exterior to the side surfaces of the protective tube, a portion of exhaust gas flowing in the direction of exhaust gas in the exhaust passage may reverse its flow direction, and flow through any openings that exist in the protective tube and exit the protective tube through apertures at the sides of the protective tube. As such, after passing the downstream surface of the protective tube at 1802, a portion of exhaust gas may turn 180 degrees back toward the sensor assembly, and may flow through the intake apertures on the downstream surface of the protective tube at 1804.

At 1806, the portion of exhaust gases may be streamed onto and across a surface of the PM sensor (e.g., PM sensor 1532 positioned within the protective tube. The portion of exhaust gases may impinge on an electrical circuit located on the surface of the PM sensor. The impingement may allow a more uniform particulate matter distribution on the electrical circuit located on the surface of the PM sensor. At 1808, the portion of exhaust gases within the protective tube may be released from exit channels on side surfaces of the protective tube. A lower static pressure at the side surfaces may assist in drawing out the portion of exhaust gases from the PM sensor assembly. Further, at 1810, the portion of exhaust gases may merge with rest of the exhaust gases flowing past the side surfaces of the PM sensor assembly in the exhaust passage.

In this way a method may comprise streaming exhaust gas flowing in an exhaust passage around a tube positioned in the exhaust passage, directing a portion of the exhaust gas through a plurality of perforations on a downstream surface of the tube, the downstream surface being normal to, and facing away from a direction of exhaust flow in the exhaust passage, flowing the portion of exhaust gas onto a particulate matter sensor located within the second inner tube, and guiding the portion of exhaust gas out of the tube and into the exhaust passage through one or more channels on side surfaces of the second inner tube, the side surfaces being tangential to the direction of exhaust flow in the exhaust passage. The streaming of the exhaust gas around the tube may result in pressure differentials between exterior surfaces of the tube, the static pressure exterior to the side surface is lower than exterior to the downstream surface, and the static pressure exterior to the downstream surface is less than exterior to an upstream surface, and wherein the tube creates narrowed region on each of two sides of the tube by decreasing cross-sectional area. The pressure differential between the downstream surface and side surfaces of the tube may induce the portion of exhaust gas to flow opposite the direction of exhaust flow in the exhaust passage back towards the downstream surface of the tube. Further in the method, the exhaust gas may be drawn into the tube at the perforations on the downstream surface of the tube, and out of the tube at the exit channels on the side surface of the tube due to the lower pressure that exists at the side surfaces of the tube relative to the downstream surface of the tube.

In this way, a particulate matter sensor may be shielded by two protective tubes that also enhance uniform deposition. The sample of exhaust gases drawn into the sensor assembly may undergo changes in flow direction which helps reduce flow rate. Further, intake apertures on the second inner tube may be sized, shaped, and positioned to optimize uniform flow of sample gases onto the particulate matter sensor surface. In one example, exhaust gas may be drawn into the sensor assembly via a plurality of circular apertures aligned along an axis parallel to a central axis of the sensor assembly. In another example, the intake apertures may be rectangular. In both of the above examples, a plurality of drainage holes may exist at the bottom of the first outer tube, so that water droplets, and larger particulates may exit the sensor assembly. In yet another example, the sensor assembly may comprise circular apertures positioned around a circumference of the outer tube of the sensor assembly near the base of the sensor assembly. As such, drainage holes may not be needed, and water droplets and larger particulates can exit directly out the intake apertures at the downstream surface of the sensor assembly. Further a technical effect of greater uniform flow impingement of sample gasses on a particulate matter sensor may be achieved by decreasing the flow speed of the exhaust gas. Upon entering the first outer tube, exhaust gas may change direction and be forced up towards to the top of the sensor assembly, before entering intake apertures, and then may flow down, and out exit channels at the bottom of the sensor assembly. Thus, by interrupting the flow path of the exhaust gas, and decreasing its speed, the uniformity of the flow on the particulate matter sensor surface may be increased. Further still, by using a particulate matter sensor assembly whose intake apertures compel changes in gas flow direction, the particulate matter sensor may be shielded from contamination by larger particulates and water droplets.

A technical effect of providing more uniform soot deposition on a particulate matter sensor in an exhaust passage with only one protective tube may also be achieved by a particulate matter sensor assembly with intake apertures on a downstream surface of the protective tube, and exit channels on side surfaces of the protective tube. Specifically, by taking advantage of the low static pressure that exists on side surfaces of the protective tube as exhaust gas flows past the protective tube, a portion of exhaust gas may be drawn into the protective tube at a downstream surface facing away from the flow of exhaust gas in an exhaust passage and may exit through the exit channels on side surfaces of the protective tube. Thus, by placing intake apertures on the downstream surface of the protective tube, and exit channels on the side surfaces of the protective tube, a portion of exhaust gas flowing past the protective tube may naturally be drawn back into the protective tube due to the lower pressure that exists exterior to the side surfaces of the protective tube. The speed of the exhaust gas entering the exhaust tube may be significantly reduced compared to the speed of the surrounding exhaust gas in the exhaust passage because the exhaust gas may change direction by 180 degrees to flow into the protective tube via the downstream intake apertures. A first technical effect of increasing the uniformity of soot deposition on the particulate matter sensor may be achieved by the decrease in exhaust gas flow speed. Further, another technical of reducing water droplet and larger particulate deposition on the particulate matter sensor is achieved by positioning intake apertures on the downstream surface of the protective tube and exit channels on side surfaces of the protective tube. Because of their larger momentum, the water droplets and larger particulates may not be able to change direction and flow back toward the protective tube after having traveled past it.

In another representation, a method may include streaming engine exhaust gas around a tube positioned in the exhaust passage, the exhaust passage outer diameter being constant along the flow from immediately upstream to immediately downstream of the tube; and drawing exhaust gas in through perforations on a downstream surface of the tube. The downstream surface may be normal to, and face away from a direction of exhaust flow in the stream. The method may further include flowing the drawn in exhaust gas onto a particulate matter sensor located within the second inner tube. The method may further include guiding the portion of exhaust gas out of the tube and into the exhaust passage through channels on side surfaces of the second inner tube, the side surfaces being tangential to the direction of exhaust flow in the exhaust passage.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
an engine exhaust passage with an upstream end coupled to an engine exhaust; and
a particulate matter sensor positioned centrally within a protective tube in the passage, the protective tube having a cylindrical tube surface with an upstream solid surface positioned to face oncoming exhaust flow that is aperture-free, and the cylindrical tube surface further having gas intake apertures located on a downstream surface of the cylindrical tube surface, and exit channels located on both a first side surface and a second side surface of the cylindrical tube surface, where the first side surface and the second side surface oppose one another, and where the first side surface, the second side surface, the upstream solid surface, and the downstream surface of the cylindrical tube surface are positioned between a top surface and a bottom surface of the cylindrical tube surface, the particulate matter sensor having an electrical circuit on a first surface positioned within the protective tube with the first surface of the particulate matter sensor facing the gas intake apertures and facing downstream, with the gas intake apertures and the exit channels being the sole openings on the cylindrical tube surface between the top surface and the bottom surface of the cylindrical tube surface, and wherein all of the exit channels located on the first side surface and the second side surface are aligned with surfaces of the particulate matter sensor that are perpendicular to the first surface of the particulate matter sensor.

2. The system of claim 1, wherein the downstream surface includes a surface normal to and facing away from a flow of exhaust gasses in the exhaust passage, the first and second side surfaces tangential to the flow of exhaust gasses in the exhaust passage.

3. The system of claim 1, wherein the gas intake apertures of the protective tube comprise a plurality of circular apertures positioned along an axis parallel to a central axis of the protective tube.

4. The system of claim 1, wherein the exit channels comprise rectangular apertures where each aperture comprises a first pair of parallel sides longer than and orthogonal to a second pair of parallel sides, the first pair of parallel sides parallel to a central axis of the protective tube.

5. The system of claim 1, wherein the exit channels comprise circular apertures positioned along an axis parallel to a central axis of the protective tube.

6. The system of claim 1, wherein the protective tube is sealed at a top with respect to vertical when coupled in an exhaust system of a vehicle traveling on a road.

7. The system of claim 1, further comprising drainage holes positioned on a bottom surface of the protective tube.

8. The system of claim 1, wherein the gas intake apertures are aligned in a single column.

9. The system of claim 8, wherein the exit channels are positioned closer to a wall of the exhaust passage to which the particulate matter sensor is coupled than the gas intake apertures.

* * * * *